US010245260B2

(12) United States Patent
Yao et al.

(10) Patent No.: US 10,245,260 B2
(45) Date of Patent: Apr. 2, 2019

(54) ORGANIC COMPOUNDS

(71) Applicant: INTRA-CELLULAR THERAPIES, INC., New York, NY (US)

(72) Inventors: Wei Yao, New Milford, NJ (US); Peng Li, New Milford, NJ (US); Robert Davis, San Diego, CA (US); Sharon Mates, New York, NY (US); Kimberly Vanover, New York, NY (US); Gretchen Snyder, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 83 days.

(21) Appl. No.: 15/660,615

(22) Filed: Jul. 26, 2017

(65) Prior Publication Data

US 2017/0319580 A1 Nov. 9, 2017

Related U.S. Application Data

(63) Continuation-in-part of application No. PCT/US2017/015178, filed on Jan. 26, 2017.

(60) Provisional application No. 62/440,130, filed on Dec. 29, 2016, provisional application No. 62/287,264, filed on Jan. 26, 2016.

(51) Int. Cl.

| | |
|---|---|
| ***A61K 9/00*** | (2006.01) |
| ***A61K 9/16*** | (2006.01) |
| ***A61K 45/00*** | (2006.01) |
| ***A61K 45/06*** | (2006.01) |
| ***A61K 31/445*** | (2006.01) |
| ***C07D 241/40*** | (2006.01) |
| ***A61K 31/4985*** | (2006.01) |

(52) U.S. Cl.

CPC ........ *A61K 31/4985* (2013.01); *A61K 9/0019* (2013.01); *A61K 9/16* (2013.01); *A61K 31/445* (2013.01); *A61K 45/00* (2013.01); *A61K 45/06* (2013.01); *C07D 241/40* (2013.01)

(58) Field of Classification Search

None

See application file for complete search history.

(56) References Cited

U.S. PATENT DOCUMENTS

| | | | |
|---|---|---|---|
| 2,490,813 | A | 12/1949 | Hughes et al. |
| 3,299,078 | A | 1/1967 | Pachter |
| 3,813,392 | A | 5/1974 | Sellstedt et al. |
| 3,914,421 | A | 10/1975 | Rajagopalan |
| 4,001,263 | A | 1/1977 | Plattner |
| 4,115,577 | A | 9/1978 | Rajagopalan |
| 4,136,145 | A | 1/1979 | Fuchs et al. |
| 4,183,936 | A | 1/1980 | Rajagopalan |
| 4,219,550 | A | 8/1980 | Rajagopalan |
| 4,238,607 | A | 12/1980 | Rajagopalan |
| 4,389,330 | A | 6/1983 | Tice et al. |
| 4,522,944 | A | 6/1985 | Doria et al. |
| 4,530,840 | A | 7/1985 | Tice et al. |
| 4,849,246 | A | 7/1989 | Schmidt |
| 4,935,419 | A | 6/1990 | Björk et al. |
| 4,971,971 | A | 11/1990 | Tokunaga et al. |
| 4,985,432 | A | 1/1991 | Tokunaga et al. |
| 5,114,976 | A | 5/1992 | Norden |
| 5,151,419 | A | 9/1992 | Perenyi et al. |
| 5,538,739 | A | 7/1996 | Bodmer et al. |
| 5,576,460 | A | 11/1996 | Buchwald et al. |
| 5,629,003 | A | 5/1997 | Horstmann et al. |
| 5,648,539 | A | 7/1997 | Goodbrand et al. |
| 5,648,542 | A | 7/1997 | Goodbrand et al. |
| 5,654,482 | A | 8/1997 | Goodbrand et al. |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,763,476 | A | 6/1998 | Delbressine et al. |
| 5,847,166 | A | 12/1998 | Buchwald et al. |
| 5,902,901 | A | 5/1999 | Goodbrand et al. |
| 5,948,430 | A | 9/1999 | Zerbe et al. |
| 6,043,370 | A | 3/2000 | Kubo et al. |
| 6,166,226 | A | 12/2000 | Buchwald et al. |
| 6,221,335 | B1 | 4/2001 | Foster |
| 6,235,936 | B1 | 5/2001 | Buchwald et al. |
| 6,307,087 | B1 | 10/2001 | Buchwald et al. |

(Continued)

FOREIGN PATENT DOCUMENTS

| | | |
|---|---|---|
| EP | 0 058 481 | 8/1982 |
| EP | 0 856 508 | 8/1998 |

(Continued)

OTHER PUBLICATIONS

Zhang et al. "The Role of Serotonin 5-HT2A Receptors in Memory and Cognition". Frontiers in Pharmacology. Oct. 2015; 6:225. (Year: 2015).*

Pine et al. "Dopamine, Time, and Impulsivity in Humans". Journal of Neuroscience. Jun. 2010; 30(26):8888-8896. (Year: 2010).*

Noble et al. "The Opioid Receptors as Targets for Drug Abuse Medication". British Journal of Pharmacology. 2015; 172:3964-3979. (Year: 2015).*

Alvir et al. Clozapine-Induced Agranulocytosis. The New England Journal of Medicine, 1993, vol. 329, No. 3, pp. 162-167.

Avendano, C., et al., "The problem of the existence of C(Ar)-H . . . N Intramolecular Hydrogen Bonds in a Family of 9-Azaphenyl-9H-carbazoles," J. Chem. Soc. Perkin Trans., vol. 2, pp. 1547-1555, (1993).

Balbach, S., et al., "Pharmaceutical evaluation of early development candidates 'the 100 mg-approach'", International Journal of Pharmaceutics, vol. 275, p. 112 (2004).

(Continued)

*Primary Examiner* — Leslie A. Royds Draper

(74) *Attorney, Agent, or Firm* — Hoxie & Associates LLC

(57) ABSTRACT

The invention relates to particular substituted heterocycle fused gamma-carbolines, their prodrugs, in free, solid, pharmaceutically acceptable salt and/or substantially pure form as described herein, pharmaceutical compositions thereof, and methods of use in the treatment of diseases involving the $5\text{-}HT_{2A}$ receptor, the serotonin transporter (SERT), pathways involving the dopamine $D_1$ and $D_2$ receptor signaling system, and/or the μ-opioid receptor.

15 Claims, 2 Drawing Sheets

(56) References Cited

U.S. PATENT DOCUMENTS

| | | | |
|---|---|---|---|
| 6,323,366 | B1 | 11/2001 | Wolfe et al. |
| 6,395,916 | B1 | 5/2002 | Buchwald et al. |
| 6,407,092 | B1 | 6/2002 | Hester et al. |
| 6,440,710 | B1 | 8/2002 | Keinan et al. |
| 6,465,693 | B2 | 10/2002 | Buchwald et al. |
| 6,541,639 | B2 | 4/2003 | Zhou et al. |
| 6,544,559 | B2 | 4/2003 | Mesens et al. |
| 6,548,493 | B1 | 4/2003 | Robichaud et al. |
| 6,552,017 | B1 | 4/2003 | Robichaud et al. |
| 6,552,024 | B1 | 4/2003 | Chen et al. |
| 6,603,008 | B1 | 8/2003 | Ando et al. |
| 6,699,852 | B2 | 3/2004 | Robichaud et al. |
| 6,713,471 | B1 | 3/2004 | Robichaud et al. |
| 6,759,554 | B2 | 7/2004 | Buchwald et al. |
| 6,762,329 | B2 | 7/2004 | Marcoux et al. |
| 6,849,619 | B2 | 2/2005 | Robichaud et al. |
| 6,849,640 | B2 | 2/2005 | Ennis et al. |
| 6,867,298 | B2 | 3/2005 | Buchwald et al. |
| 6,888,032 | B2 | 5/2005 | Buchwald et al. |
| 6,946,560 | B2 | 9/2005 | Buchwald et al. |
| 7,026,498 | B2 | 4/2006 | Buchwald et al. |
| 7,071,186 | B2 | 7/2006 | Robichaud et al. |
| 7,081,455 | B2 | 7/2006 | Robichaud et al. |
| 7,109,339 | B2 | 9/2006 | Lee et al. |
| 7,115,784 | B2 | 10/2006 | Buchwald et al. |
| 7,183,282 | B2 | 2/2007 | Robichaud et al. |
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 7,375,226 | B2 | 5/2008 | Jolidon et al. |
| 7,462,641 | B2 | 12/2008 | Igo et al. |
| 7,517,990 | B2 | 4/2009 | Ito et al. |
| 7,592,454 | B2 | 9/2009 | Lee et al. |
| 7,614,727 | B2 | 11/2009 | Hori |
| 7,645,752 | B2 | 1/2010 | McDevitt et al. |
| 7,998,971 | B2 | 8/2011 | Barlow et al. |
| 8,309,722 | B2 | 11/2012 | Tomesch et al. |
| 8,309,772 | B2 | 11/2012 | Weiner et al. |
| 8,414,922 | B2 | 4/2013 | Bryson et al. |
| 8,461,148 | B2 | 6/2013 | Hollander |
| 8,475,793 | B2 | 7/2013 | Malefyt et al. |
| 8,598,119 | B2 | 12/2013 | Mates et al. |
| 8,603,514 | B2 | 12/2013 | Yang et al. |
| 8,648,077 | B2 | 2/2014 | Tomesch et al. |
| 8,652,378 | B1 | 2/2014 | Yang et al. |
| 8,697,700 | B2 | 4/2014 | Surman et al. |
| 8,779,139 | B2 | 7/2014 | Tomesch et al. |
| 8,791,138 | B2 | 7/2014 | Seeman et al. |
| 8,835,459 | B2 | 9/2014 | Kottayil et al. |
| 8,900,497 | B2 | 12/2014 | Yang et al. |
| 8,900,498 | B2 | 12/2014 | Yang et al. |
| 8,906,277 | B2 | 12/2014 | Yang et al. |
| 8,993,572 | B2 | 3/2015 | Mates et al. |
| 9,108,340 | B2 | 8/2015 | Yang et al. |
| 9,168,258 | B2 | 10/2015 | Mates et al. |
| 9,199,995 | B2 | 12/2015 | Tomesch et al. |
| 9,216,175 | B2 | 12/2015 | Amancha et al. |
| 9,315,504 | B2 | 4/2016 | Tomesch et al. |
| 9,371,324 | B2 | 6/2016 | Mates et al. |
| 9,393,192 | B2 | 7/2016 | Yam et al. |
| 9,427,412 | B2 | 8/2016 | Bryson et al. |
| 9,428,506 | B2 | 8/2016 | Mates et al. |
| 9,567,327 | B2 | 2/2017 | Xiong et al. |
| 9,586,960 | B2 | 3/2017 | Tomesch et al. |
| 9,616,061 | B2 | 4/2017 | Mates et al. |
| 9,708,322 | B2 | 7/2017 | Li et al. |
| 9,745,300 | B2 | 8/2017 | Mates et al. |
| 9,751,883 | B2 | 9/2017 | Tomesch et al. |
| 9,956,227 | B2 | 5/2018 | Vanover et al. |
| 2001/0008942 | A1 | 7/2001 | Buchwald et al. |
| 2004/0034015 | A1 | 2/2004 | Robichaud et al. |
| 2004/0092534 | A1 | 5/2004 | Yam et al. |
| 2004/0127482 | A1 | 7/2004 | Robichaud et al. |
| 2004/0142970 | A1 | 7/2004 | Chung et al. |
| 2004/0180875 | A1 | 9/2004 | Lee et al. |
| 2004/0209864 | A1 | 10/2004 | Robichaud et al. |
| 2004/0220178 | A1 | 11/2004 | Robichaud et al. |
| 2005/0166771 | A1 | 8/2005 | Gygi et al. |
| 2005/0222209 | A1 | 10/2005 | Zeldis et al. |
| 2005/0239768 | A1 | 10/2005 | Lee et al. |
| 2006/0128713 | A1 | 6/2006 | Jolidon et al. |
| 2006/0178362 | A1 | 8/2006 | Robichaud et al. |
| 2006/0205787 | A1 | 9/2006 | Muller et al. |
| 2007/0082929 | A1 | 4/2007 | Gant et al. |
| 2007/0197695 | A1 | 8/2007 | Potyen et al. |
| 2007/0203120 | A1 | 8/2007 | McDevitt et al. |
| 2008/0069885 | A1 | 3/2008 | Mesens et al. |
| 2008/0132552 | A1 | 6/2008 | Kleinman et al. |
| 2008/0280941 | A1 | 11/2008 | Lourtie et al. |
| 2009/0076159 | A1 | 3/2009 | Czarnik |
| 2009/0202631 | A1 | 8/2009 | Yam et al. |
| 2009/0209608 | A1 | 8/2009 | Czarnik |
| 2010/0113781 | A1 | 5/2010 | Tomesch et al. |
| 2010/0159033 | A1 | 6/2010 | Gant et al. |
| 2010/0298382 | A1 | 11/2010 | Seeman |
| 2011/0071080 | A1 | 3/2011 | Mates et al. |
| 2011/0112105 | A1 | 5/2011 | Tomesch et al. |
| 2011/0263592 | A1 | 10/2011 | Xiong et al. |
| 2012/0157469 | A1 | 6/2012 | Surman et al. |
| 2012/0196814 | A1 | 8/2012 | Gong et al. |
| 2013/0202692 | A1 | 8/2013 | Mates et al. |
| 2014/0050783 | A1 | 2/2014 | Mates et al. |
| 2014/0080816 | A1 | 3/2014 | Koolman et al. |
| 2014/0323491 | A1 | 10/2014 | Tomesch et al. |
| 2014/0364609 | A1 | 12/2014 | Tomesch et al. |
| 2015/0072964 | A1 | 3/2015 | Mates et al. |
| 2015/0079172 | A1 | 3/2015 | Mates et al. |
| 2015/0080404 | A1 | 3/2015 | Mates et al. |
| 2015/0166540 | A1 | 6/2015 | Mates et al. |
| 2015/0166542 | A1 | 6/2015 | Kjer-Nielsen |
| 2016/0031885 | A1 | 2/2016 | Li et al. |
| 2016/0194325 | A1 | 7/2016 | Tomesch et al. |
| 2016/0310502 | A1 | 10/2016 | Vanover et al. |
| 2016/0354315 | A1 | 12/2016 | Li |
| 2017/0037048 | A1 | 2/2017 | Mates et al. |
| 2017/0114037 | A1 | 4/2017 | Davis et al. |
| 2017/0183350 | A1 | 6/2017 | Mates et al. |
| 2017/0189398 | A1 | 7/2017 | Mates et al. |
| 2017/0283417 | A1 | 10/2017 | Li et al. |
| 2018/0044337 | A1 | 2/2018 | Tomesch et al. |
| 2018/0200256 | A1 | 7/2018 | Vanover et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 564 671 | 1/2005 |
| EP | 1 539 115 | 6/2005 |
| GB | 1476087 | 6/1977 |
| GB | 2145422 | 3/1985 |
| WO | WO 1994/024125 | 10/1994 |
| WO | WO 1995/013814 | 5/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/059129 | 8/2002 |
| WO | WO 2002/085838 | 10/2002 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2006/034187 | 3/2006 |
| WO | WO 2006/081251 | 8/2006 |
| WO | WO 2007/025103 | 3/2007 |

(56) References Cited

FOREIGN PATENT DOCUMENTS

| | | |
|---|---|---|
| WO | WO 2007/084841 | 7/2007 |
| WO | WO 2008/112280 | 9/2008 |
| WO | WO 2009/017836 | 2/2009 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2017/117514 | 7/2017 |
| WO | WO 2017/132408 | 8/2017 |
| WO | WO 2017/165755 | 9/2017 |
| WO | WO 2017/165843 | 9/2017 |

OTHER PUBLICATIONS

Bastin, R., et al.,"Salt Selection and Optimisation Procedures for Pharmaceutical New Chemical Entities", Organic Process and Research Development, vol. 4, No. 5, pp. 427-435 (2000).

Beletskaya, I.P., et al., "Pd- and Cu-catalyzed selective arylation of benzotriazole," Tetrahedron Letters, vol. 39, pp. 5617-5620, (1998).

Berger, J., et al., "Synthesis of some conformationally restricted analogs of fentanyl." Journal of Medicinal Chemistry, vol. 20, No. 4, p. 600-602. 1977.

Boger, D., et al., "Inverse Electron Demand Diels-Alder Reactions of Heterocyclic Aza Dienes. Studies on the Toal Synthesis of Lavendamycin: Investigative Studies on the Preparation of the CDE β-Carboline Ring System and AB Quinoline-5,8-quinone Ring System" J. Org. Chem., vol. 50, p. 5782-5789, (1985).

Bowman, W.R., et al., "Copper (1) Catalysed Aromatic Nucleophilic Substitution: A Mechanistic and Synthetic Comparison with the $S_{RN}$ 1 Reaction", Tetrahedron Letters, vol. 25(50) p. 5821-5824, (1984).

Bowman, W.R., et al.,"Synthesis of 1H-quinazoline-4-ones using intramolecular aromatic nucelophilic substitution," ARKIVOC, vol. x, pp. 434-442 (2003).

Bowman, W.R., et al., "Intramolecular Aromatic Substitution ($S_{RN}$1) Reactions—Use of Entrainment for the Preparation of Benzothiazoles," Tetrahedron Letters, vol. 23, pp. 5093-5096, (1982).

Bremner et al., "Neuroimaging of Posttraumatic Stress Disorder", Psychiatric Annals Journal, vol. 28, Issue 8, p. 445-450, (1998).

Bryan-Lluka, L. J. et al., "Potencies of haloperidol metabolites as inhibitors of the human noradrenaline, dopamine and serotonin transporters in transfected COS-7 cells", Naunyn-Shemiedeberg's Arch Pharmacol, 1999, vol. 360, pp. 109-115.

Byrn, S., et al., "Pharmaceutical Solids: A Strategic Approach to Regulatory Considerations", Pharmaceutical Research, vol. 12, No. 7, p. 945-954 (1995).

Crawford, K., et al., "Copper-Catalyzed amidations of bromo substituted furans and thiophenes", Tetrahedron Letters, vol. 43, p. 7365-7368, (2002).

Darmani, N. A., et al., "Do Functional Relationships Exist Between 5-$HT_{1A}$ and 5-$HT_2$ Receptors?" Pharmacology and Biochemistry & Behavior, vol. 36, p. 901-906, (1990).

Davis et al. "ITI-007 demonstrates brain occupancy at serotonin 5-$HT_{2A}$ and dopamine $D_2$ receptors and serotonin transporters using positron emission tomography in healthy volunteers," Psychopharmacology, Published Online Apr. 7, 2015, vol. 232, pp. 2863-2872.

Davis et al. "ITI-007 in the treatment of schizophrenia: from novel pharmacology to clinical outcomes," Expert Review of Neurotherapeutics, vol. 16, No. 6, pp. 601-614 (2016).

Evindar, G., et al., "Copper- and Palladium-Catalyzed Intramolecular Aryl Guanidinylation: An Efficient Method for the Synthesis of 2-Aminobenzimidazoles", Organic Letters, vol. 5, No. 2, p. 133-136, (2003).

Ezquerra, J., et al., "Efficient Reagents for the Synthesis of 5-, 7-, and 5, 7-Substitued Indoles Starting from Aromatic Amines: Scope and Limitations", J. Org. Chem., vol. 61, p. 5804-5812, (1996).

Fawcett, J., "Posttraumatic Stress Disorder, Stress, and Happiness", Psychiatric Annals Journal, vol. 28, Issue 8, p. 427-428, (1998).

Fee, W.W., et al., "Copper (II)-promoted solvolyses of nickel (II) complexes III. Tetradentate Schiff base ligands containing various diamine segments," Aust. J. Chem., vol. 26, pp. 1475-1485, (1973).

Ferreira, I., et al., "Novel synthetic routes to thienocarbazoles via palladium or copper catalyzed amination or amidation of arylhalides and intramolecular cyclization", Tetrahedron, vol. 58, p. 7943-7949, (2002).

Finet, J-P., et al., "Recent advances in ullmann reaction: copper (II) diacetate catalysed N-,O- and S-acylation involving polycoordinate heteroatomic derivatives," Current Organic Chemistry, vol. 6, pp. 597-626, (2002).

Foster, P.S., et al., "Acetylcholinesterase inhibitors reduce spreading activation in dementia," Neuropsychologia, vol. 50, p. 2093-2099, (2012).

Friedman, M.J.., "Current and Future Drug Treatment for Post-traumatic Stress Disorder Patients", Psychiatric Annals Journal, vol. 28, Issue 8, p. 464-468, (1998).

Goodbrand, H.B., et al., "Ligand-Accelerated catalysis of the Ullmann condensation: Application to hole conducting triarylamines," J. Org. Chem., vol. 64, pp. 670-674, (1999).

Grant, D., "Theory and Origin and Polymorphism", Polymorphism in Pharmaceutical Solids, Chapter 1, p. 1-10 (1999).

Guillory, J.K., "Generation of Polymorphs, Hydrates, Solvates, and Amorphous Solids", Polymorphism in Pharmaceutical Solids, Chapter 5, p. 183-226 (1999).

Hackam, D., et al., "Translation of Research Evidence from Animals to Humans", JAMA, vol. 296(14), p. 1731-1732 (2006).

Hamann, B., et al., "Systematic Variation of Bidentate Ligands used in Aryl Halide Amination. Unexpected Effects of Steric, Electronic, and Geometric Perturbations", J. Am. Chem. Soc., vol. 120, p. 3694-3703, (1998).

Harbert, C.A. et al., "Neuroleptic Activity in 5-Aryltetrahydro-y-carbolines", J. Med. Chem., vol. 23, pp. 635-643 (1980).

Hartwig, J., "Palladium-catalyzed amination of aryl halides: Mechanism and rational catalyst design," Synlett, pp. 329-340, (1996).

Harvey, B.H., et al., "Serotonin and Stress: Protective or Malevolent Actions in the Biobehavioral Response to Repeated Trauma?" Annals of the New York Academy of Sciences, vol. 1032, p. 267-272; DOI: 10.1196/annals.1314.035 (2004).

Hassan, J., et al., "Aryl-aryl bond formation one century after the discovery of the ullmann reaction," Chem. Rev., vol. 102, pp. 1359-1469, (2002).

Haynes, "Occurrence of Pharmaceutically Acceptable Anions and Cations in the Cambridge Structural Database", Journal of Pharmaceutical Sciences, vol. 94, No. 10, p. 2111-2120 (2005).

International Preliminary Report on Patentability for International Application No. PCT/US2013/036514 dated Oct. 14, 2014.

International Search Report issued in International Application No. PCT/US2008/003340, dated Aug. 8, 2008, 3 pages.

International Search Report issued in International Application No. PCT/US2009/001608, dated Apr. 27, 2009, 3 pages.

International Search Report issued in International Application No. PCT/US2009/003261, dated Jul. 16, 2009, 3 pages.

International Search Report issued in International Application No. PCT/US2011/00719, dated Jul. 5, 2011, 3 pages.

International Search Report issued in International Application No. PCT/US2013/036512, dated Aug. 19, 2013, 4 pages.

International Search Report issued in International Application No. PCT/US2013/036514, dated Aug. 16, 2013, 3 pages.

International Search Report issued in International Application No. PCT/US2013/036515, dated Aug. 13, 2013, 3 pages.

International Search Report issued in International Application No. PCT/US2017/015178, dated Apr. 12, 2017, 3 pages.

Ito, T., et al., "Studies of organic catalytic reactions. VI. The function of pyridine and copper in the Rosenmund-von Braun reaction," Bulletin of the Chemical Society of Japan vol. 41, pp. 419-423, (1968).

(56) References Cited

OTHER PUBLICATIONS

Izrayelit, L., "Schizoaffective Disorder and PTSD Successfully Treated With Olanzapine and Supportive Psychotherapy", Psychiatric Annals Journal, vol. 28, Issue 8, p. 424-426, (1998).
Jain et al., "Polymorphism in Pharmacy", Indian Drugs, 23(6), 315-316 (1986).
Ji, J. et al., "Selective amination of polyhalopyridines catalyzed by a palladium-xantphos complex," Organic Letters, vol. 5, No. 24, pp. 4611-4614, (2003).
Jordan, V.C. "Tamoxifen: A Most Unlikely Pioneering Medicine", Nature Reviews: Drug Discovery, vol. 2, p. 205-213, (2003).
Kametani, T., et al., "A Novel Synthesis of Indole Derivatives", Heterocycles, vol. 14 (3), p. 277-280, (1980).
Kang, S-K., et al., "Copper-catalyzed N-arylation of aryl iodides with benzamides or nitrogen heterocycles in the presence of ethylendiamine," Synlett, No. 3, pp. 427-430, (2002).
Kay, S.R., et al., "The Positive and Negative Syndrome Scale (PANSS) for Schizophrenia," Schizophrenia Bulletin, vol. 13, Issue 2, pp. 261-276, (1987).
Kessler, R.C., et al., "Lifetime Prevalence and Age-of-Onset Distributions of DSM-IV Disorders in the National Comorbidity Survey Replication," Arch Gen Psychiatry; vol. 62, pp. 593-602, (2005).
Khorana, N., et al., "Gamma-Carbolines: Binding at 5-HT5A Serotonin Receptors," Bioorganic & Medicinal Chemistry, vol. 11, Issue 5, 6, pp. 717-722, p. 718 Table 1, (2003).
Kiyomori, A., et al., "An efficient copper-catalyzed coupling of aryl halides with imidazoles," Tetrahedron Letters, vol. 40, pp. 2657-2660, (1999).
Klapars, A., et al., "A general and efficient copper catalyst for the amidation of aryl halides and the N-arylation of nitrogen heterocycles," J. Am. Chem. Soc., vol. 123, No. 25, pp. 7727-7729, (2001).
Klapars, A., et al., "A general and efficient copper catalyst for the amidation of aryl halides," J. Am. Chem. Soc., vol. 124, pp. 7421-7428, (2002).
Kondratov, S.A., et al., "Nucelophilic substitution in the aromatic series. Lv. Reaction of o-nitrochlorobenzene with ammonia in the presence of copper compounds," Zhurnal Organidreskoi Khimii, vol. 51(11), pp. 2387-2390, (1979).
Koppel, J., et al., "Optimal Treatment of Alzheimer's Disease Psychosis: Challenges and Solutions," Neuropsychiatric Disease and Treatment, vol. 10, pp. 2253-2262, (2014).
Kwong, F.Y., et al., "Mild and efficient copper-catalyzed amination of aryl bromides with primary alkylamines," Organic Letters, vol. 5, No. 6, pp. 793-796, (2003).
Lebert, F., et al., "Trazodone in Fronto-Temporal Dementia," Research and Practice in Alzheimer's Disease, vol. 11, 356-360, (2006).
Lee, T., et al. "Novel, Highly Potent, Selective 5-$HT_{2A}$/$D_2$ Receptor Antagonists as Potential Atypical Antipsychotics," Bioorg. Med. Chem. Lett., vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders," Journal of Medicinal Chemistry, vol. 57, p. 2670-2682 (2014).
Lieberman, J.A., et al., "ITI-007 for the Treatment of Schizophrenia: A 4-Week Randomized, Double-Blind, Controlled Trial," Biol. Psychiatry, 79(12), pp. 952-961, (2015).
Lin, Y-T., et al., "Dosage and Duration of Antipsychotic Treatment in Demented Outpatients with Agitation or Psychosis," Journal of the Formosan Medical Association, vol. 114, pp. 147-153, (2015).
Lipschitz, D.S., et al., "Childhood Posttraumatic Stress Disorder: A Review of Neurobiologic Sequelae," Psychiatric Annals Journal, vol. 28, Issue 8, p. 452-457, (1998).
Lopez, et al., "Psychiatric Symptoms Vary with the Severity of Dementia in Probably Alzheimer's Disease," J. Neuropsychiatry Clin. Neurosc., vol. 15(3), pp. 346-353, (2003).
Louie, J., et al., "Palladium-Catalyzed Synthesis of Arylamines from Aryl Halides, Mechanistic Studies lead to Coupling in the Absence of Tin Reagents," Tetrahedron Letters, vol. 36(21), p. 3609-3612, (1995).
Lounkine, E., et al.,"Formal Concept Analysis for the Identification of Molecular Fragment Combinations Specific for Active and Highly Potent Compounds," J. Med. Chem., vol. 51, No. (17), 5342-5348, (2008).
Madhusoodanan, S., et al., "Pharmacological Management of Behavioral Symptoms Associated with Dementia," World J. Psychiatr., vol. 4, No. 4, pp. 72-79, (2014).
March et al, "Advanced Organic Chemistry; Reactions, Mechanisms and Structures," Fourth Edition, pp. 910-911 (1992).
Marcoux, J-F., et al., "A general copper-catalyzed synthesis of diaryl ethers," J. Am. Chem. Soc., vol. 119, pp. 10539-10540, (1997).
Mohamed, S., et al., "Pharmacotherapy of PTSD in the U.S. Department of Veterans Affairs: diagnostic- and symptom-guided drug selection," J. Clin. Psychiatry, vol. 69, pp. 959-965, (2008).
Morgan, C.A., et al., "Acoustic Startle in Individuals With Posttraumatic Stress Disorder," Psychiatric Annals Journal, vol. 28, Issue 8, p. 430-434, (1998).
Mulrooney, C., et al., "Recent developments in copper-catalyzed n-arylation with aryl halides," Essay—University of Pennsylvania (2004).
Murakami et al., "Fischer Indolization of Ethyl Pyruvate 2-[2-(Trifluoromethyl) phenyl]-phenylhydrazone and New Insight into the Mechanism of the Goldberg Reaction." Chem. Pharm. Bull, vol. 43(8), p. 1281-1286, (1995).
Nagai, Y., et al., "Synthesis of 2,3,4,4a,5,9b-hexahydro-1H-pyrido[4,3-b] indole derivatives and their central nervous system activities." Journal of Medicinal Chemistry, vol. 22, No. 6, p. 677-683. 1979.
Newman, A.W., et al., "Solid-state analysis of the active pharmaceutical ingredient in drug products," Drug Discovery Today, vol. 8, No. 9, 898-903 (2003).
Pond, S.M. et al., "Stereospecific reduction of haloperidol in human tissues," Biochemical Pharmacology, vol. 44 (5), p. 867-871 (1992).
Protective Groups in Organic Synthesis, Third Edition, John Wiley & Sons, Inc., p. 494-505, (1999).
Rackova, L., et al., "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548, (2006).
Sadighi, J.P., et al., "A highly active palladium catalyst system for the arylation of anilines," Tetrahedron Letters, vol. 39, pp. 5327-5330, (1998).
Savjani, K., et al., "Drug Solubility: Importance and Enhancement Techniques," International Scholarly Research Network Pharmaceutics, vol. 2012, pp. 1-10, (2012).
Sigel, H., et al., "Tenary Complexes in Solution," Inorganic Chemistry, vol. 13, No. 2, p. 462-465 (1974).
Singhal, D., et al., "Drug polymorphism and dosage form design: a practical perspective", Advanced Drug Delivery Reviews, vol. 56, pp. 335-347 (2004).
Skoog, D., et al., "Principles of Instrumental Analysis, $4^{th}$ Edition", p. 577 (1992).
Smith, A.D., et al., "Oxford Dictionary of Biochemistry and Molecular Biology," Oxford University Press, p. 145, (1997).
Snyder, G.L., et al., "Functional profile of a novel modulator of serotonin, dopamine, and glutamate neurotransmission," Psychopharmacology, vol. 232, p. 605-621 (2015) Published online Aug. 2014, DOI 10.1007/s00213-014-3704-1.
Southwick, S.M., et al., "Neuroendocrine Alterations in Posttraumatic Stress Disorder," Psychiatric Annals Journal, vol. 28, Issue 8, p. 436-442, (1998).
Sugahara, M., et al., "A Facile Copper-Catalyzed Ullman Condensation: N-Arylation of Heterocyclic Compounds Containing an—NHCO—Moiety," Chem. Pharm. Bull., vol. 45(4), p. 719-721, (1997).
Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).

(56) References Cited

OTHER PUBLICATIONS

Tariot, et al., "Memantine Treatment in Patients with Moderate to Severe Alzheimer Disease Already Receiving Donepezil: A Randomized Controlled Trail," JAMA, vol. 291, No. 3, pp. 317-324, (2004).
Wagaw, S., et al., "A palladium-catalyzed method for the preparation of indoles via the Fischer indole synthesis," Journal of the American Chemical Society, vol. 121, No. 44, pp. 10251-10263, (1999).
Weschules, D., et al., "Acetylcholinesterase Inhibitor and N-Methyl-D-Aspartic Acid Receptor Antagonist Use among Hospice Enrollees with a Primary Diagnosis of Dementia," Journal of Palliative Medicine, vol. 11, No. 5, 738-745 (2008).
Wiese, M., "DSC Detection of Polymorphism in Pharmaceutical Anhdrous Dexamethasone Acetate," TA Instruments, TA302:1-4 (2002).
Wolfe, J.P., et al., "An improved catalyst system for aromatic carbon-nitrogen bond formation: The possible involvement of bis(phosphine) palladium complexes as key intermediates," JACS, vol. 118, pp. 7215-7216, (1996).
Wolfe, J.P. et al., "Intramolecular palladium-catalyzed aryl amination and aryl amidation," Tetrahedron, vol. 52, No. 21, pp. 7525-7546, (1996).
Wolter, M., et al., "Synthesis of N-aryl hydrazides by copper-catalyzed coupling of hydrazides with aryl iodides," Organic Letters, vol. 3, No. 23, pp. 3803-3805, (2001).
Written Opinion of the International Searching Authority for International Application No. PCT/US2013/036514 dated Aug. 16, 2013, 4 pages.
Yamada, K., et al., "A mild copper-mediated intramolecular amination of aryl halides," Synlett, No. 2, pp. 231-234, (2002).
Yang, B.H., "The development of efficient protocols for the palladium-catalyzed cyclization reactions of secondary amides and carbamates," Organic Letters, vol. 1, No. 1, pp. 35-37, (1999).
Yudofsky, S., et al., "Propranolol in the Treatment of Rage and Violent Behavior in Patients with Chronic Brain Syndromes," Am. J. Psychiatry, vol. 138, p. 218-220, (1981).
Zhang, Z., et al., "Highly efficient copper-catalyzed N-arylation of alkylamines with aryl iodides using phosphoramidite as ligand," Catalysis Communications, vol. 6, p. 784-787, (2005).
Angst, J., et al., "Prevalence and Characteristics of Undiagnosed Bipolar Disorders in Patients with a Major Depressive Episode," Arch Gen Psychiatry, vol. 68, No. 8, (2011), pp. 791-799.
Baille, T.A., "The Use of Stable Isotopes in Pharmacological Research," Pharmacol. Reviews, vol. 33, No. 2, pp. 81-132, (1981).
Bennett, J.C., et al., "Cecil Textbook of Medicine," 20th Edition, vol. 1, pp. 1004-1010, (1996).
Borghans, et al., "Animal Models for Posttraumatic Stress Disorder: An Overview of What is Used in Research," *World J. Psychiatr.*, vol. 5, No. 4, pp. 387-396, (2015); DOI: 10.5498/wjp.v5.i4.387.
Browne, T.R., "Stable Isotope Techniques in Early Drug Development: An Economic Evaluation," J. Clin. Pharmacol., vol. 38, pp. 213-220, (1998).
Caira, et al., "Crystalline Polymorphism of Organic Compounds," Topics in Current Chemistry, vol. 198, p. 163-203, (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, pp. 653-657, (1987).
Dyck, L.E., et al., "Effects of Deuterium Substitution on the Catabolism of β-Phenylethylamine: An In Vivo Study," Journal of Neurochemistry, vol. 46, Issue 2, pp. 399-404, (1986).
Fitzgerald, R.J., et al., "Inhibition of Caries in Hamsters by 2-Deoxy-D-Glucose," J. Dent, (1977), vol. 56, No. 11, pp. 1431 (1 page).
Foster, A.B., "Deuterium Isotope Effects in the Metabolism of Drugs and Xenobiotics: Implications for Drug Design," 1985, Advances in Drug Research, vol. 14, pp. 1-40.
Gouyette, A., "Synthesis of Deuterium-labelled Elliptinium and its Use in Metabolic Studies," Biomedical and Environmental Mass Spectrometry, vol. 15, pp. 243-247, (1988).
Haskins, N.J., "The Application of Stable Isotopes in Biomedical Research," Biological Mass Spectrometry, vol. 9, No. 7, pp. 269-277, (1982).
Honma, S., et al., "The Metabolism of Roxatidine Acetate Hydrochloride: Liberation of Deuterium from the Piperidine Ring during Hydroxylation," Drug Metabolism and Disposition, vol. 15, No. 4, pp. 551, (1987).
International Search Report for International Patent Application PCT/US15/24340, prepared by the International Search Authority, dated Jun. 25, 2015, 2 pages.
International Search Report for International Patent Application PCT/US15/24345, prepared by the International Search Authority, dated Jun. 25, 2015, 3 pages.
Juorio, A.V., et al., "Effects of Acute and Chronic Phenelzine on Regional Monoamine Metabolism in Rats and its Potentiation by Deuterium Substitution," Naunyn-Schmiedeberg's Archives of Pharmacology, vol. 333, No. 3, pp. 240-245, (1986); Abstract only.
Lammers, L., "Risperidone long-acting injection in Schizophrenia Spectrum Illnesses compared to first generation depot antipsychotics in an outpatient setting in Canada," BMC Psychiatry, vol. 13, No. 155, 9 pages, (2013).
Marek, G.J., et al., "Synergistic Action of 5-$HT_{2A}$ Antagonists and Selective Serotonin Reuptake Inhibitors in Neuropsychiatric Disorder," Neuropsychopharmacology, (2003), vol. 28, pp. 402-412.
Perlis, R.H., et al., "Clinical Features of Bipolar Depression Versus Major Depressive Disorder in Large Multicenter Trials," Am J Psychiatry, vol. 163, (2006), pp. 225-231.
Pieniaszek, H.J., et al., "Moricizine Bioavailability via Simultaneous Dual, Stable Isotope Administration: Bioequivalence Implications," J. Clin. Pharmacol., vol. 39, pp. 817-825, (1999).
PubChem, OPEN Chemistry Database, Compound Summary for CID-22036753, pp. 4, (2007), 12 pages.
Rainer, M.K., "Risperidone long-acting injection: a review of its long term safety and efficacy," Neuropsychiatric Disease and Treatment, vol. 4, No. 5, pp. 919-927 (2008).
Renner, J.A., Jr., "Management of Psychiatric Medications in Patients Receiving Buprenorphine/Naloxone," PCSS MAT Training Providers' Clinical Support System for Medical Assisted Treatment, Last Updated: Nov. 28, 2013, 4 pages.
Ramaswamy, et al., "Failed Efficacy of Ziprasidone in the Treatment of Post-Traumatic Stress Disorder," *Contemporary Clinical Trials Communications*, vol. 2, pp. 1-5, (2016).
"Securities," Bennett v. Alkermes, Inc., at http://securities.stanford.edu/filings-documents/1029/ALKS03-01/20031029_r01c_0312091.pdf (retrieved from the internet on Jun. 13, 2017) (2003).
Semla, et al., "Off-Label Prescribing of Second-Generation Antipsychotics to Elderly Veterans with Posttraumatic Stress Disorder and Dementia," *J. Am. Geriatr. Soc.*, vol. 65, pp. 1789-1795, (2017); DOI: 10.1111/jgs.14897.
Tonn, G.R., et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes," Biological Mass Spectrometry, vol. 22, pp. 633-642, (1993).
Tung, R., "The Development of Deuterium-Containing Drugs," Innovations in Pharmaceutical Technology, vol. 32, (2010), pp. 1-4.
Wolen, R. L., "The Application of Stable Isotopes to Studies of Drug Bioavailability and Bioequivalence," J. Clin. Pharmacol., vol. 26, pp. 419-424, (1986).

* cited by examiner

ORGANIC COMPOUNDS

RELATED APPLICATIONS

This application is a Continuation-in-Part under 35 U.S.C. § 111 of International Application PCT/US2017/015178, filed Jan. 26, 2017, designating the United States and claiming the benefit of U.S. Provisional Application No. 62/440,130, filed Dec. 29, 2016, and U.S. Provisional Application No. 62/287,264, filed Jan. 26, 2016, the contents of each of which are incorporated herein by reference in their entireties.

FIELD OF THE INVENTION

The invention relates to particular substituted heterocycle fused gamma-carbolines, their prodrugs, in free, solid, pharmaceutically acceptable salt and/or substantially pure form as described herein, pharmaceutical compositions thereof, and methods of use in the treatment of diseases involving the 5-$HT_{2A}$ receptor, the serotonin transporter (SERT), pathways involving dopamine $D_1$ and $D_2$ receptor signaling systems, and/or the μ-opioid receptor, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; mood disorders; drug dependencies, such as opiate dependency and alcohol dependency, drug withdrawal symptoms, and other psychiatric and neurological conditions, as well as to combinations with other agents. In addition, such compounds and compositions are useful in methods of treatment of obsessive-compulsive disorder (OCD), obsessive-compulsive personality disorder (OCPD), and related disorders. In some embodiments, the disease or disorders may include treatment-resistant depression, cocaine dependency, and/or amphetamine dependency.

BACKGROUND OF THE INVENTION

Substituted heterocycle fused gamma-carbolines are known to be agonists or antagonists of 5-$HT_2$ receptors, particularly 5-$HT_{2A}$ and 5-$HT_{2C}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-$HT_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. PCT/US08/03340 (WO 2008/112280) and U.S. application Ser. No. 10/786,935 also disclose methods of making substituted heterocycle fused gamma-carbolines and uses of these gamma-carbolines as serotonin agonists and antagonists useful for the control and prevention of central nervous system disorders such as addictive behavior and sleep disorders.

In addition, WO/2009/145900 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-$HT_{2A}$ receptors without affecting or minimally affecting dopamine $D_2$ receptors, thereby useful for the treatment of sleep disorders without the side effects associated with high occupancy of the dopamine $D_2$ pathways or side effects of other pathways (e.g., $GABA_A$ receptors) associated with convention sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains. WO 2009/114181 also discloses of methods of preparing toluenesulfonic acid addition salt crystals of these substituted heterocycle fused gamma-carbolines.

Obsessive-compulsive disorder (OCD) and related disorders, have become highly prevalent and are difficult to treat. OCD is estimated to affect about 2.3% of people at some point in their lives, and during a given year, it is estimated than 1.2% of people worldwide suffer from the disorder. Half of people who suffer from OCD begin to show symptoms before the age of 20, which can seriously affect their ability to obtain an adequate and effective education. Without effective treatment, however, the disease can last for decades. The mainstay of pharmacologic OCD treatment is with selective serotonin reuptake inhibitors (SSRIs). A second line of therapy is with antipsychotic agents, such as clomipramine, risperidone, quetiapine and olanzapine. A significant number of patients either do not respond to these agents, or cannot handle the side effects caused by these agents. More recently, it has been reported that the opioid analgesic tramadol may be effective in treating OCD. Opiates operate by an entirely different pathway from traditional OCD treatment agents, so they offer the possibility of treatment for people who cannot take the traditional serotonergic agents or for whom these agents are ineffective. However, strong opiate agents can be addictive, and their use may be contraindicated in some patients. There thus remains an urgent need for new treatments for OCD and related disorders.

SUMMARY OF THE INVENTION

The present disclosure provides Compounds of Formula I that are useful for the treatment or prophylaxis of central nervous system disorders. In a first aspect, the present disclosure relates to a compound (Compound I) of Formula I:

Formula I

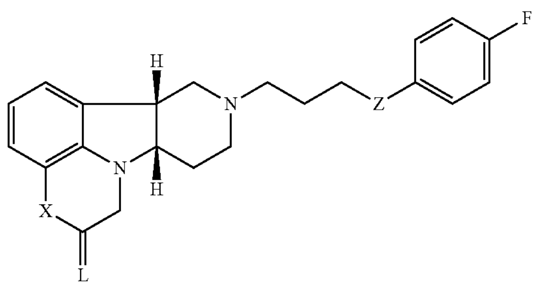

wherein:

X is —NH— or —$N(CH_3)$—;

L is selected from O, NH, $NR^a$, and S;

Z is —CH(O—$R_1$)—, —O— or —C(═O)—;

$R_1$ is H, —C(O)—$C_{1-21}$ alkyl (e.g., —C(O)—$C_{1-5}$ alkyl, —C(O)—$C_{6-15}$ alkyl or —C(O)—$C_{16-21}$ alkyl), preferably said alkyl is a straight chain, optionally saturated or unsaturated and optionally substituted with one or more hydroxy or $C_{1-22}$ alkoxy (e.g., ethoxy) groups, for example $R_1$ is C(O)—$C_3$ alkyl, —C(O)$C_6$ alkyl, —C(O)—$C_7$ alkyl, —C(O)—$C_9$ alkyl, —C(O)—$C_{11}$ alkyl, —C(O)—$C_{13}$ alkyl or —C(O)—$C_{15}$ alkyl;

$R^a$ is:

halogen, $C_{1-4}$ alkyl, $C_{2-4}$ alkenyl, $C_{2-4}$ alkynyl, or $C_{3-6}$ cycloalkyl, each of which can be independently substituted with up to three independently selected $R^b$ groups, for example $C_{-1-3}$haloalkyl or $C_{1-3}$hydroxyalkyl; or aryl optionally substituted with up to five independently selected $R^b$; and each $R^b$ is independently selected from H, halogen, $NH_2$, $NO_2$, OH, C(O)OH, CN, $SO_3$, and $C_{1-4}$ alkyl;

in free or salt form, for example in an isolated or purified free or salt form.

The present disclosure provides additional exemplary embodiments of the Compound of Formula I, in free or salt form, for example in an isolated or purified free or salt form, including:

1.1 Compound I, wherein L is —O—;

1.2 Compound I or 1.1, wherein Z is —CH(O—$R_1$)—;

1.3 Compound I or 1.1, wherein Z is —C(═O)—;

1.4 Compound I, wherein L is NH.

1.5 Compound I, wherein L is $NR^a$;

1.6 Compound I, wherein L is S;

1.7 Compound I or any of 1.1-1.6, in solid form, for example in solid salt form;

1.8 Compound I or any of 1.1-1.7, wherein Z is —CH(O—$R_1$)—;

1.9 Compound I, or any of 1.1-1.7, wherein Z is —C(═O)—;

1.10 Compound I, or any of 1.1-1.7, wherein Z is —O—;

1.11 Compound I or any of 1.1-1.10, wherein X is —NH—;

1.12 Compound I or any of 1.1-1.10, wherein X is —N($CH_3$)—;

1.13 Compound I or any of 1.1-1.12, wherein L is —O— and X is —N($CH_3$)—;

1.14 Compound I or any of 1.1-1.12, wherein L is —O— and X is —NH—;

1.15 Compound 1.13, wherein Z is —C(═O)—;

1.16 Compound 1.14, wherein Z is —C(═O)—;

1.17 Compound I or any of 1.1-1.14, wherein Z is —CH(O—$R_1$)— and $R_1$ is H;

1.18 Compound I or any of 1.1-1.14, wherein Z is —CH(O—$R_1$)— and $R_1$ is —C(O)—$C_{1-5}$ alkyl, —C(O)—$C_{6-15}$ alkyl or —C(O)—$C_{16-21}$ alkyl;

1.19 Compound I or any of 1.1-1.14, wherein Z is —CH(O—$R_1$)— and $R_1$ is selected from the group consisting of C(O)—$C_3$ alkyl, —C(O)$C_6$ alkyl, —C(O)—$C_7$ alkyl, —C(O)—$C_9$ alkyl, —C(O)—$C_{11}$ alkyl, —C(O)—$C_{13}$ alkyl or —C(O)—$C_{15}$ alkyl; for example, wherein $R^1$ is acetyl, ethylcarbonyl, or propylcarbonyl;

1.20 Compound I or any of 1.1-1.12 or 1.17-1.19, wherein L is $NR^a$, and wherein $R^a$ is: halogen, $C_{1-4}$ alkyl, $C_{2-4}$ alkenyl, $C_{2-4}$ alkynyl, or $C_{3-6}$ cycloalkyl, each of which can be independently substituted with up to three independently selected $R^b$ groups; or wherein $R^a$ is aryl optionally substituted with up to five independently selected $R^b$; wherein $R^b$ is independently selected from H, halogen, $NH_2$, $NO_2$, OH, C(O)OH, CN, $SO_3$, and $C_{1-4}$ alkyl;

1.21 Compound 1.20, wherein $R^a$ is $C_{1-4}$ alkyl or $C_{3-6}$ cycloalkyl, optionally substituted with up to three independently selected $R^b$ groups;

1.22 Compound 1.20, wherein $R^a$ is aryl, optionally substituted with up to three independently selected $R^b$ groups;

1.23 Compound 1.20, wherein $R^a$ is selected from the group consisting of methyl, ethyl, propyl, butyl, isopropyl, isobutyl, sec-butyl, or phenyl;

1.24 Compound I, or any of 1.1-1.14 or 1.17-1.23, wherein Z is —CH(O—$R_1$)—; and said carbon atom CH in the group —CH(O—$R_1$)— has either the R configuration or the S configuration, or a mixture thereof;

1.25 Compound 1.24, wherein the carbon atom CH is substantially present in either the R configuration or the S configuration, e.g., wherein the diastereomer having the R configuration or the S configuration at this carbon is present in greater than 70% diastereomeric excess, for example, greater than 75%, or greater than 80%, or greater than 85%, or greater than 90%, or greater than 95%, or greater than 97%, or greater than 98% or greater than 99%, diastereomeric excess.

1.26 Compound I, or any of 1.1-1.25, wherein the compound is selected from the group consisting of:

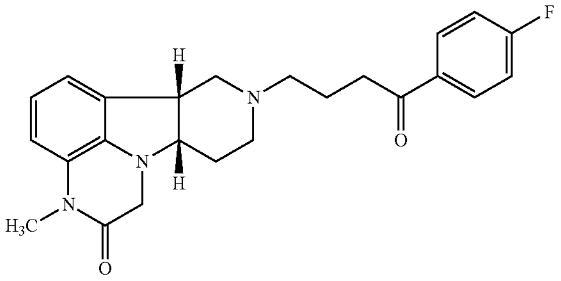

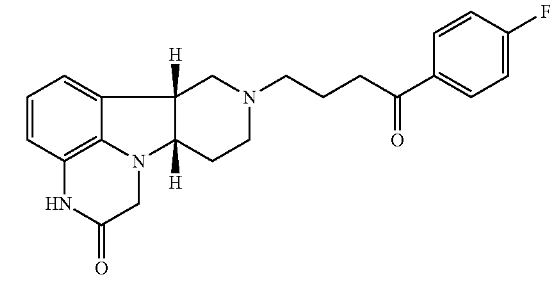

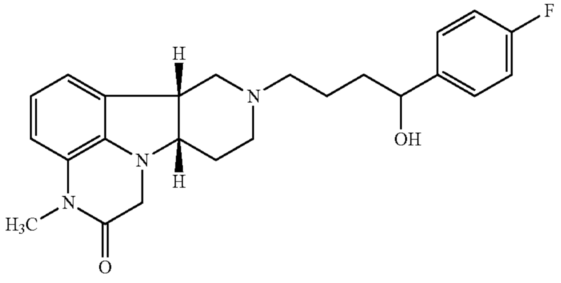

-continued
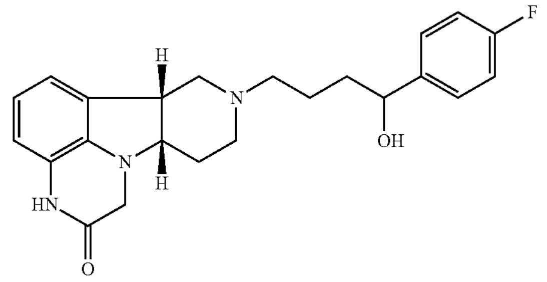
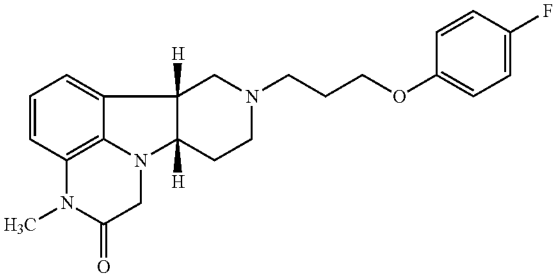
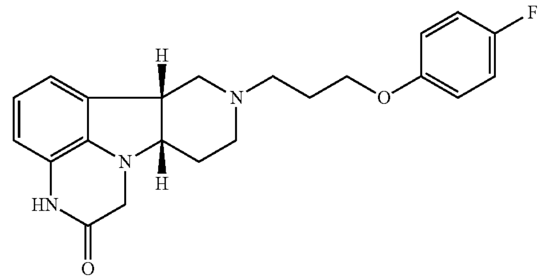
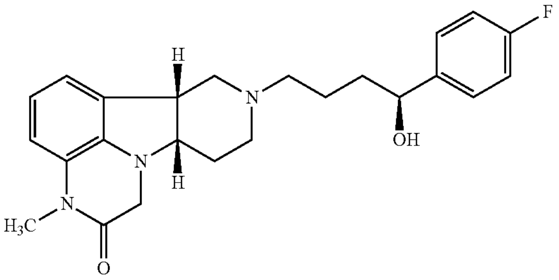
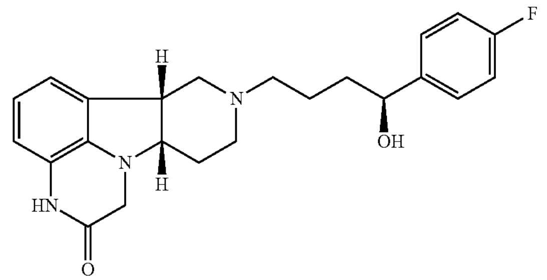
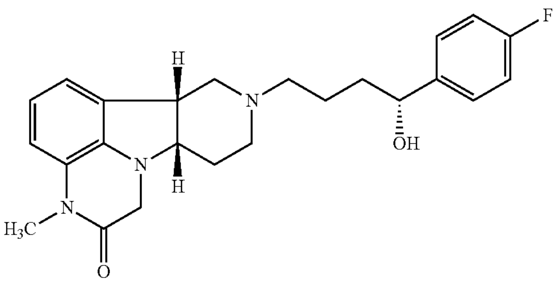
-continued
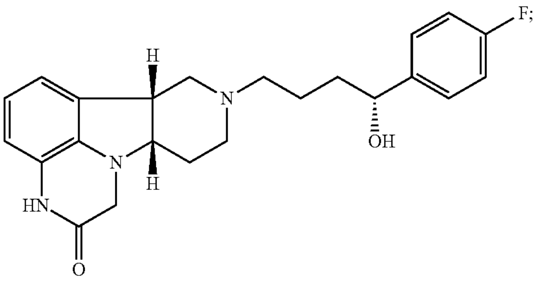
1.27 Compound I, or any of 1.1-1.25, wherein the compound is selected from the group consisting of:
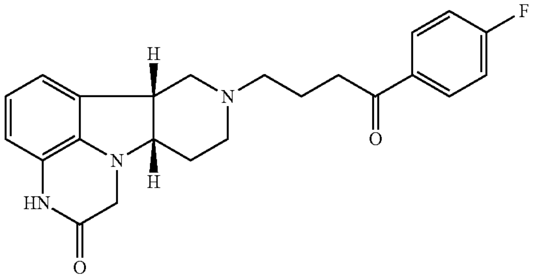
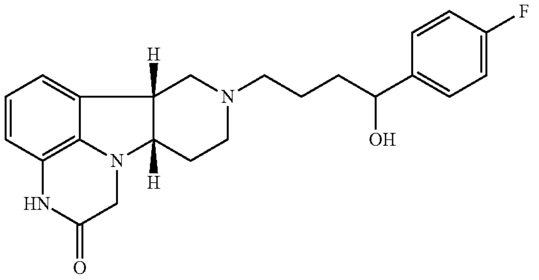
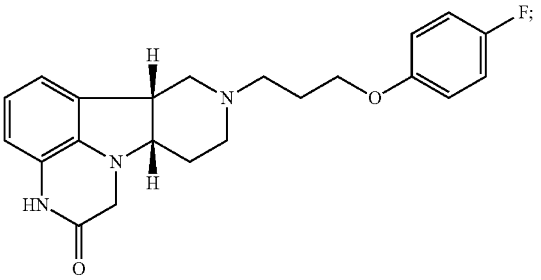
1.28 Compound I, or any of 1.1-1.28, in free form;
1.29 Compound I, or any of 1.1-1.28 in salt form, e.g., pharmaceutically acceptable salt form;
1.30 Compound I or any of 1.1-1.29 in solid form.
in free or salt form, for example in an isolated or purified free or salt form.

In a second aspect, the present disclosure relates to a compound (Compound II) of Formula II:

Formula II

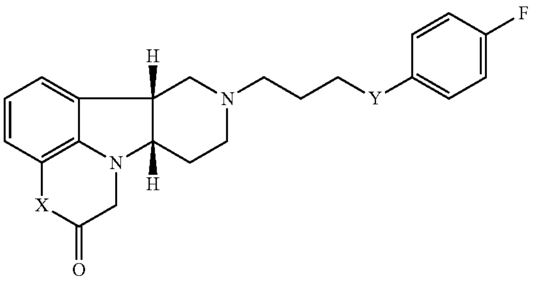

wherein:

X is —NH— or —N($CH_3$)—;

Y is —CH(O—$R_1$)— or —C(═O)—;

$R_1$ is H, —C(O)—$C_{1-21}$ alkyl (e.g., —C(O)—$C_{1-5}$ alkyl, —C(O)—$C_{6-15}$ alkyl or —C(O)—$C_{16-21}$ alkyl), preferably said alkyl is a straight chain, optionally saturated or unsaturated and optionally substituted with one or more hydroxy or $C_{1-22}$ alkoxy (e.g., ethoxy) groups, for example $R_1$ is C(O)—$C_3$ alkyl, —C(O)$C_6$ alkyl, —C(O)—$C_7$ alkyl, —C(O)—$C_9$ alkyl, —C(O)—$C_{11}$ alkyl, —C(O)—$C_{13}$ alkyl or —C(O)—$C_{15}$ alkyl;

in free or salt form, for example in an isolated or purified free or salt form.

The present disclosure provides additional exemplary embodiments of the Compound of Formula II, in free or salt form, for example in an isolated or purified free or salt form, including:

2.1 Compound II, wherein X is —NH—;

2.2 Compound II, wherein X is —N($CH_3$)—;

2.3 Compound II, or 2.1-2.4, wherein Y is —C(═O)—;

2.4 Compound II, wherein Y is —CH(O—$R_1$)—; i.e., having the Formula II-A:

Formula II-A

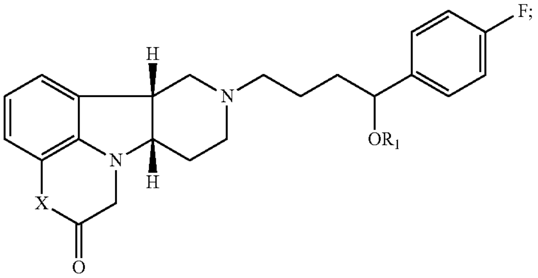

2.5 Compound II, or 2.1-2.4, wherein Y is —CH(O—$R_1$)—;

2.6 Compound II, wherein X is NH and Y is —C(═O)—; i.e., having the Formula II-B:

Formula II-B

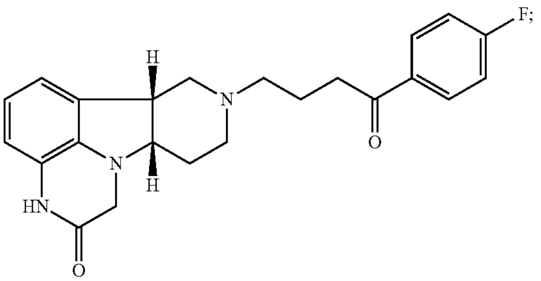

2.7 Compound II, wherein X is —NH— and Y is —CH(O—$R_1$)—;

2.8 Compound II, wherein X is —NH— and Y is —CH(O—$R_1$)—, wherein $R_1$ is H; i.e., having the Formula II-C:

Formula II-C

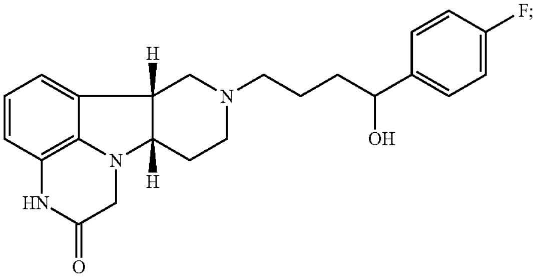

2.9 Compound II, wherein X is —N($CH_3$)— and Y is —C(═O)—; i.e., having the Formula II-D:

Formula II-D

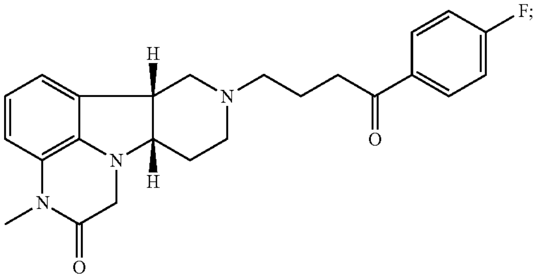

2.10 Compound II, wherein X is —N($CH_3$)— and Y is —CH(O—$R_1$)—;

2.11 Compound II, wherein X is —$N(CH_3)$— and Y is —CH(O—$R_1$)—, wherein $R_1$ is H; i.e., having the Formula II-E:

Formula II-E

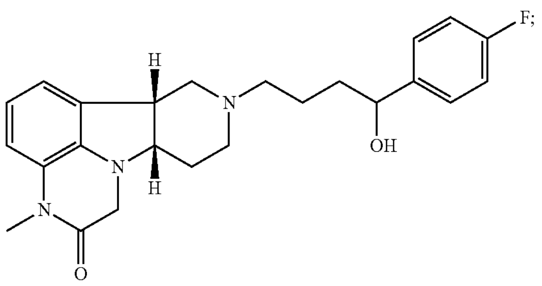

2.12 Compound II or any of 2.1-2.11, in solid form, for example in solid salt form.

In a third aspect, the present disclosure relates to a compound (Compound III) of Formula III:

Formula III

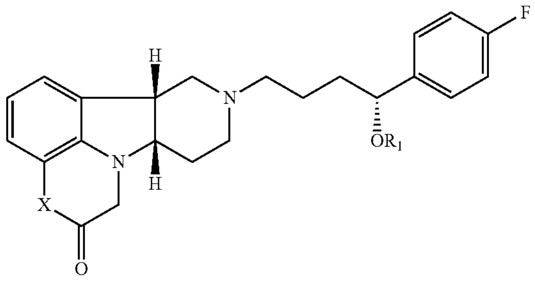

wherein:

X is —NH— or —$N(CH_3)$—;

$R_1$ is H, —C(O)—$C_{1-21}$ alkyl (e.g., —C(O)—$C_{1-5}$ alkyl, —C(O)—$C_{6-15}$ alkyl or —C(O)—$C_{16-21}$ alkyl), preferably said alkyl is a straight chain, optionally saturated or unsaturated and optionally substituted with one or more hydroxy or $C_{1-22}$ alkoxy (e.g., ethoxy) groups, for example $R_1$ is C(O)—$C_3$ alkyl, —C(O)$C_6$ alkyl, —C(O)—$C_7$ alkyl, —C(O)—$C_9$ alkyl, —C(O)—$C_{11}$ alkyl, —C(O)—$C_{13}$ alkyl or —C(O)—$C_{15}$;

in free or salt form, for example in an isolated or purified free or salt form.

The present disclosure provides additional exemplary embodiments of the Compound of Formula III, in free or salt form, for example in an isolated or purified free or salt form. including:

3.1 Compound III, wherein $R_1$ is H; i.e., having the Formula III-A:

Formula III-A

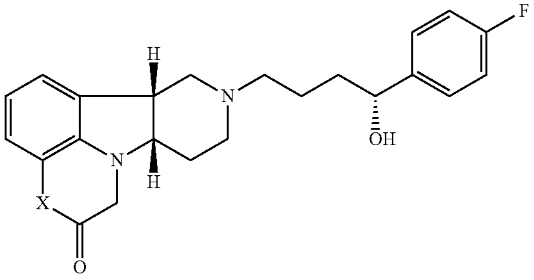

in free or salt form, for example in an isolated or purified free or salt form;

3.2 Compound III or 3.1, wherein X is —NH—;

3.3 Compound III or 3.1, wherein X is —$N(CH_3)$—;

3.4 Compound 3.1, wherein X is —NH—; i.e., having the Formula III-B:

Formula III-B

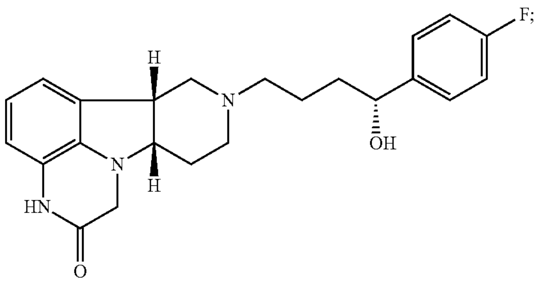

3.5 Compound 3.1, wherein X is —$N(CH_3)$—; i.e., having the Formula III-C:

Formula III-C

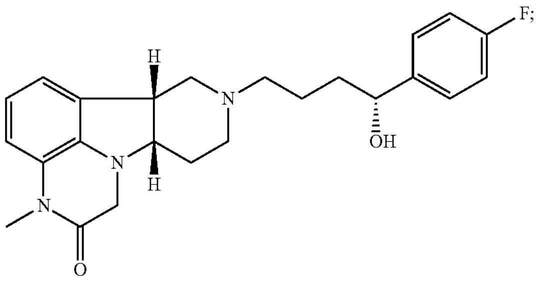

3.6 Compound III or any of 3.1-3.5, wherein the Compound has a diastereomeric excess of greater than 70%;

3.7 Compound III or any of 3.1-3.6, wherein the Compound has a diastereomeric excess of greater than 80%;

3.8 Compound III or any of 3.1-3.7, wherein the Compound has a diastereomeric excess of greater than 90%;

3.9 Compound III or any of 3.1-3.8, wherein the Compound has a diastereomeric excess of greater than 95%;

3.10 Compound III or any of 3.1-3.9, wherein the Compound is in substantially pure diastereomeric form (i.e., substantially free from other diastereomers)

3.11 Compound III or any of 3.1-3.10, in solid form, for example in solid salt form.

In a fourth aspect, the present disclosure relates to a compound (Compound IV) of Formula IV:

Formula IV

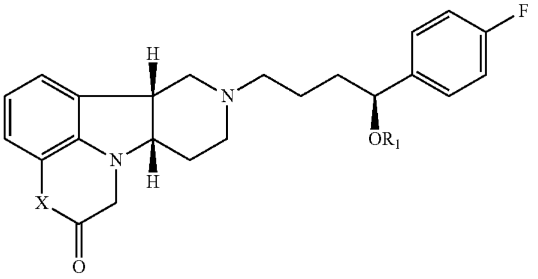

wherein:

X is —NH— or —N($CH_3$)—;

$R_1$ is H, —C(O)—$C_{1-21}$ alkyl (e.g., —C(O)—$C_{1-5}$ alkyl, —C(O)—$C_{6-15}$ alkyl or —C(O)—$C_{6-21}$ alkyl), preferably said alkyl is a straight chain, optionally saturated or unsaturated and optionally substituted with one or more hydroxy or $C_{1-22}$ alkoxy (e.g., ethoxy) groups, for example $R_1$ is C(O)—$C_3$ alkyl, —C(O)$C_6$ alkyl, —C(O)—$C_7$ alkyl, —C(O)—$C_9$ alkyl, —C(O)—$C_{11}$ alkyl, —C(O)—$C_{13}$ alkyl or —C(O)—$C_{15}$ alkyl;

in free or salt form, for example in an isolated or purified free or salt form.

The present disclosure provides additional exemplary embodiments of the Compound of Formula IV, in free or salt form, for example in an isolated or purified free or salt form, including:

4.1 Compound IV, wherein $R_1$ is H; i.e., having the Formula IV-A:

Formula IV-A

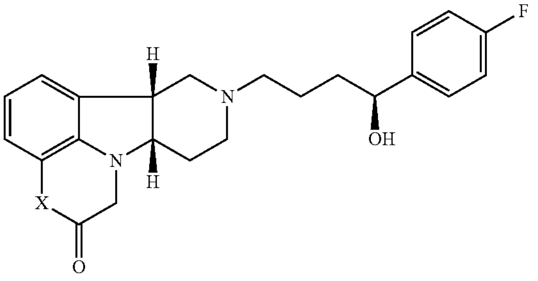

in free or salt form, for example in an isolated or purified free or salt form.

4.2 Compound IV or 4.1, wherein X is —NH—;

4.3 Compound IV or 4.1, wherein X is —N($CH_3$)—;

4.4 Compound 4.1, wherein X is —NH—; i.e., having the Formula IV-B:

Formula IV-B

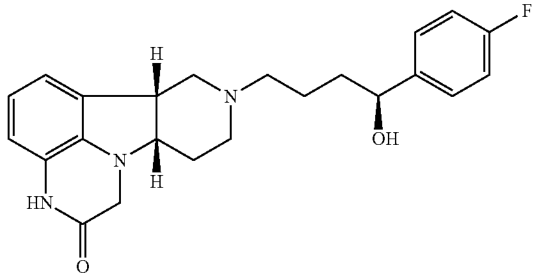

4.5 Compound 4.1, wherein X is —N($CH_3$)—; i.e., having the Formula IV-C:

Formula IV-C

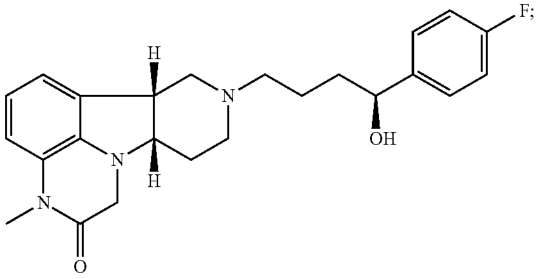

4.6 Compound IV or any of 4.1-4.5, wherein the Compound has a diastereomeric excess of greater than 70%

4.7 Compound IV or any of 4.1-4.6, wherein the Compound has a diastereomeric excess of greater than 80%

4.8 Compound IV or any of 4.1-4.7, wherein the Compound has a diastereomeric excess of greater than 90%

4.9 Compound IV or any of 4.1-4.8, wherein the Compound has a diastereomeric excess of greater than 95%

4.10 Compound IV or any of 4.1-4.9, wherein the Compound is in substantially pure diastereomeric form (i.e., substantially free from other diastereomers);

4.11 Compound IV or any of 4.1-4.10, in solid form, for example in solid salt form.

In a fifth aspect, the present disclosure provides each of the foregoing Compound I or 1.1-1.30, Compound II or 2.1-2.12, Compound III or 3.1-3.11, or Compound IV or 4.1-4.11 (hereinafter collectively "Compounds of Formulas I-IV et seq." or "compounds of the disclosure") in free or pharmaceutically acceptable salt form. The present disclosure provides additional exemplary embodiments of the Compounds of Formulas I-IV et seq., including:

5.1 Compounds of Formulas I-IV et seq., wherein the salt is an acid addition salt selected from hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;

5.2 Compounds of Formulas I-IV et seq., wherein the salt is fumaric acid addition salt;

5.3 Compounds of Formulas I-IV et seq., wherein the salt is phosphoric acid addition salt;

5.4 Compounds of Formulas I-IV et seq., wherein the salt is a toluenesulfonic acid addition salt;

5.5 Any of 5.1-5.4 wherein the salt is in solid form.

In a sixth aspect, the present disclosure provides a pharmaceutical composition (Pharmaceutical Composition 6) comprising a compound according to any one of Compound I or 1.1-1.30, Compound II or 2.1-2.12, Compound III or 3.1-3.11, or Compound IV or 4.1-4.11 (collectively, Compounds of Formulas I-IV et seq. or compounds of the disclosure), e.g., in admixture with a pharmaceutically acceptable diluent or carrier. The present disclosure provides additional exemplary embodiments of Pharmaceutical Composition 6, including:

6.1 Pharmaceutical Composition 6, comprising Compound I or any of 1.1-1.30;

6.2 Pharmaceutical Composition 6, comprising Compound II or any of 2.1-2.12;

6.3 Pharmaceutical Composition 6, comprising Compound III or any of 3.1-3.11;

6.4 Pharmaceutical Composition 6, comprising Compound IV or any of 4.1-4.11;

6.5 Pharmaceutical Composition 6 or any of 6.1-6.4, wherein the Compound of Formula I-IV et seq. is in solid form;

6.6 Pharmaceutical Composition 6 or any of 6.1-6.5, wherein the Compound of Formulas I-IV et seq. is in pharmaceutically acceptable salt form as described in Compounds 5.1-5.5;

6.7 Pharmaceutical Composition 6 or any of 6.1-6.6, wherein the Compound of Formulas I-IV et seq. is in admixture with a pharmaceutically acceptable diluent or carrier.

In a preferred embodiment, the Pharmaceutical Composition of the present disclosure comprises a Compound of Formula II-A, II-B, or II-C, in free or pharmaceutically acceptable salt form, in admixture with a pharmaceutically acceptable diluent or carrier. In another preferred embodiment, the Pharmaceutical Composition of the present disclosure comprises a Compound of Formula III-A, III-B or III-C in free or pharmaceutically acceptable salt form, in admixture with a pharmaceutically acceptable diluent or carrier. In another preferred embodiment, the Pharmaceutical Composition of the present disclosure comprises a Compound of Formula IV-A, IV-B or IV-C in free or pharmaceutically acceptable salt form, in admixture with a pharmaceutically acceptable diluent or carrier.

In a further embodiment, the Pharmaceutical Compositions of the present disclosure, are for a sustained or delayed release, e.g., depot, formulation. In one embodiment, the depot formulation (Depot Formulation 6.8) is the Pharmaceutical Composition of any of 6.1-6.7, preferably in free or pharmaceutically acceptable salt form, and preferably in admixture with a pharmaceutically acceptable diluent or carrier, e.g., providing sustained or delayed release as an injectable depot.

In a further embodiment, the Depot Composition (Depot Composition 6.9) comprises Pharmaceutical Composition of any of 6.1-6.7, wherein $R_1$ is a —C(O)—$C_{6-15}$alkyl, in free or pharmaceutically acceptable salt form, in admixture with a pharmaceutically acceptable diluent or carrier.

In another aspect, the present disclosure provides Pharmaceutical Composition 6.10, which is Pharmaceutical Composition 6 or any of 6.1-6.9, wherein the Compound of Formulas I-IV et seq. is in a polymeric matrix. In one embodiment, the Compound of the present disclosure is dispersed or dissolved within the polymeric matrix. In a further embodiment, the polymeric matrix comprises standard polymers used in depot formulations such as polymers selected from a polyester of a hydroxyfatty acid and derivatives thereof, or a polymer of an alkyl alpha-cyanoacrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly (glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide).

For example, in one embodiment of Pharmaceutical Composition 6.10, the Compound is the Compound of Formula I, wherein X is —NH— or —N($CH_3$)— and Y is —C(═O)— or —C(H)(OH)—, in free or pharmaceutically acceptable salt form. In another example of Pharmaceutical Composition 6.10, the Compound is the Compound of Formula II-A, II-B, or II-C, in free or pharmaceutically acceptable salt form, in admixture with a pharmaceutically acceptable diluent or carrier. In another example of Pharmaceutical Composition 6.10, the Compound is the Compound of Formula III-A, III-B or III-C in free or pharmaceutically acceptable salt form, in admixture with a pharmaceutically acceptable diluent or carrier. In another example of Pharmaceutical Composition 6.10, the Compound is the Compound of Formula IV-A, IV-B or IV-C in free or pharmaceutically acceptable salt form, in admixture with a pharmaceutically acceptable diluent or carrier. In another embodiment of each of the foregoing examples of Pharmaceutical Composition 6.10, the polymeric matrix comprises a poly(d,l-lactide-co-glycolide).

The (Pharmaceutical) Compositions 6 and 6.1-6.10 are particularly useful for sustained or delayed release, wherein the Compound of the present disclosure is released upon degradation of the polymeric matrix. These Compositions may be formulated for controlled- and/or sustained-release of the Compounds of the present disclosure (e.g., as a depot composition) over a period of up to 180 days, e.g., from about 14 to about 30 to about 180 days. For example, the polymeric matrix may degrade and release the Compounds of the present disclosure over a period of about 30, about 60 or about 90 days. In another example, the polymeric matrix may degrade and release the Compounds of the present disclosure over a period of about 120, or about 180 days.

In still another embodiment, the Pharmaceutical Compositions of the present disclosure, for example the depot composition of the present disclosure, e.g., Pharmaceutical Composition 6.10, is formulated for administration by injection.

In a seventh aspect, the present disclosure provides the Compounds of Formulas I-IV et seq. as hereinbefore described, in an osmotic controlled release oral delivery system (OROS), which is described in WO 2000/35419 and EP 1 539 115 (U.S. Pub. No. 2009/0202631), the contents of each of which applications are incorporated by reference in their entirety. Therefore in one embodiment of the seventh aspect, the present disclosure provides a pharmaceutical composition or device comprising (a) a gelatin capsule containing a Compound of any of Formulae I-IV et seq. in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Composition P.1)

In another embodiment, the invention provides a pharmaceutical composition comprising a gelatin capsule containing a liquid, the Compound of Formulas I-IV et seq. in free or pharmaceutically acceptable salt form or a Pharmaceutical Composition of the Invention, e.g., any of Pharmaceutical Composition 6 or 6.1-6.10, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Composition P.2)

In still another embodiment of the seventh aspect, the invention provides a composition comprising a gelatin capsule containing a liquid, the Compound of Formulas I-IV et seq. in free or pharmaceutically acceptable salt form or a Pharmaceutical Composition of the Invention, e.g., any of Pharmaceutical Composition 6 or 6.1-6.10, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice. (Composition P.3)

In still another embodiment of the seventh aspect, the invention provides a composition comprising a gelatin capsule containing a liquid, the Compound of Formulas I-IV et seq. in free or pharmaceutically acceptable salt form or a Pharmaceutical Composition of the Invention, e.g., any of Pharmaceutical Composition 6 or 6.1-6.10, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment of the seventh aspect, the Compound of the present disclosure in the Osmotic-controlled Release Oral delivery System (i.e., in Composition P.1-P.4) is in a liquid formulation, which formulation may be neat, liquid active agent, liquid active agent in a solution, suspension, emulsion or self-emulsifying composition or the like.

Further information on Osmotic-controlled Release Oral delivery System composition including characteristics of the gelatin capsule, barrier layer, an expandable layer, a semipermeable layer; and orifice may be found in WO 2000/35419, the contents of which are incorporated by reference in their entirety.

Other Osmotic-controlled Release Oral delivery System for the Compound of Formulas I-IV et seq. or the Pharmaceutical Composition of the present disclosure may be found in EP 1 539 115 (U.S. Pub. No. 2009/0202631), the contents of which are incorporated by reference in their entirety. Therefore, in another embodiment of the seventh aspect, the invention provides a composition or device comprising (a) two or more layers, said two or more layers comprising a first layer and a second layer, said first layer comprises the Compound of Formulas I-IV et seq., in free or pharmaceutically acceptable salt form, or a Pharmaceutical Composition as herein before described said second layer comprises a polymer; (b) an outer wall surrounding said two or more layers; and (c) an orifice in said outer wall. (Composition P.5)

Composition P.5 preferably utilizes a semi-permeable membrane surrounding a three-layer-core: in these embodiments the first layer is referred to as a first drug layer and contains low amounts of drug (e.g., the Compound of Formulas I-IV et seq.) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers. (Composition P.7)

In a particular embodiment, the invention provides Composition P.7 wherein the first drug layer comprising salt and the second drug layer containing no salt. Composition P.5-P.7 may optionally comprise a flow-promoting layer between the membrane and the drug layers.

Compositions P.1-P.7 will generally be referred to as Osmotic-controlled Release Oral delivery System Composition.

In an eighth aspect, the invention provides a method (Method 1) for the treatment or prophylaxis of a central nervous system disorder, comprising administering to a patient in need thereof a Compound of Formulas I-IV et seq. or a Pharmaceutical Composition 6 or 6.1-6.10 or P.1-P.7, for example Method 1 wherein the compound or composition administered is:

1.1 Compound I or any of 1.1-1.30, in free or pharmaceutically acceptable salt form;

1.2 Compound II or any of 2.1-2.12, in free or pharmaceutically acceptable salt form;

1.3 Compound III or any of 3.1-3.11, in free or pharmaceutically acceptable salt form;

1.4 Compound IV or any of 4.1-4.11, in free or pharmaceutically acceptable salt form;

1.5 The Compounds of Embodiment 5 or any of 5.1-5.5;

1.6 Compound of Formula II-A, II-B, or II-C in free or pharmaceutically acceptable salt form, in admixture with a pharmaceutically acceptable diluent or carrier;

1.7 Compound of Formula III-A, III-B or III-C, in free or pharmaceutically acceptable salt form, in admixture with a pharmaceutically acceptable diluent or carrier;

1.8 Compound of Formula IV-A, IV-B or IV-C, in free or pharmaceutically acceptable salt form, in admixture with a pharmaceutically acceptable diluent or carrier;

1.9 a Pharmaceutical Composition as described by any of Compositions 6 and 6.1-6.10;

1.10 a Pharmaceutical Composition comprising a Compound of Formula II-A, II-B, or II-C, in free or pharmaceutically acceptable salt form, in admixture with a pharmaceutically acceptable diluent or carrier;

1.11 a Pharmaceutical Composition comprising a Compound of Formula III-A, III-B or III-C, in free or pharmaceutically acceptable salt form, in admixture with a pharmaceutically acceptable diluent or carrier;

1.12 a Pharmaceutical Composition comprising a Compound of Formula IV-A, IV-B or IV-C, in free or pharmaceutically acceptable salt form, in admixture with a pharmaceutically acceptable diluent or carrier;

1.13 Depot Composition as described in Depot Composition 6.09 or 6.10;

1.14 Pharmaceutical Composition P.1-P.7;

1.15 Osmotic-controlled Release Oral delivery System Composition as hereinbefore described;

In a further embodiment of the eighth aspect, the present disclosure provides Method 1 or any of Methods 1.1-1.15, wherein the method is further as described as follows:

1.16 Method 1 or any of Methods 1.1-1.15, wherein the central nervous system disorder is a disorder selected from a group consisting of obesity, anxiety, depression (for example refractory depression and MDD), psychosis (including psychosis associated with dementia, such as hallucinations in advanced Parkinson's disease or paranoid delusions), schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, gastrointestinal disorders such as dysfunction of the gastrointestinal tract motility, and dementia, for example dementia of Alzheimer's disease or of Parkinson's disease; mood disorders; and drug dependencies, for example, opiate dependency and/or alcohol dependency, or withdrawal from drug or alcohol dependency (e.g., opiate dependency); or binge eating disorder;

1.17 Method 1 or any of Methods 1.1-1.16, wherein the central nervous system disorder is a disorder involving serotonin 5-$HT_2A$, dopamine D2 receptor system and/or serotonin reuptake transporter (SERT) pathways as similarly described in WO/2009/145900, the contents of which are herein incorporated by reference in their entirety;

1.18 Method 1 or any of Methods 1.1-1.17, wherein the central nervous system disorder is a disorder involving the t-opioid receptor;

1.19 Method 1 or any of Methods 1.1-1.18, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; (4) sleep disorders associated with psychosis, e.g., schizophrenia or Parkinson's disease; and (5) substance addiction, substance use disorders and/or substance-induced disorders, optionally wherein the patient suffers from residual symptoms of anxiety or anxiety disorder;

1.20 Method 1 or any of Methods 1.1-1.18, wherein the central nervous system disorder is psychosis, e.g., schizophrenia and said patient is a patient suffering from depression;

1.21 Method 1 or any of Methods 1.1-1.20, wherein said patient is unable to tolerate the side effects of conventional antipsychotic drugs, e.g., chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone and ziprasidone;

1.22 Method 1 or any of Methods 1.1-1.20, wherein said patient is unable to tolerate the side effects of conventional antipsychotic drugs, e.g., haloperidol, aripiprazole, clozapine, olanzapine, quetiapine, risperidone, and ziprasidone;

1.23 Method 1 or any of Methods 1.1-1.22, wherein said disorder is depression and said patient is a patient suffering from psychosis, e.g., schizophrenia, or Parkinson's disease;

1.24 Method 1 or any of Methods 1.1-1.22, wherein said disorder is sleep disorder and said patient is suffering from depression;

1.25 Method 1 or any of Methods 1.1-1.22, wherein said one or more disorders is sleep disorder and said patient is suffering from psychosis, e.g., schizophrenia;

1.26 Method 1 or any of Methods 1.1-1.22, wherein said one or more disorders is sleep disorder and said patient is suffering from Parkinson's disease;

1.27 Method 1 or any of Methods 1.1-1.22, wherein said one or more disorders is sleep disorder and said patient is suffering from depression and psychosis, e.g., schizophrenia, or Parkinson's disease.

1.28 Method 1 or any of 1.1-1.27, wherein said patient is suffering from a drug dependency disorder, optionally in conjunction with any preceding disorders, for example, wherein said patient suffers from opiate dependency and/or alcohol dependency, or from withdrawal from drug or alcohol dependency, optionally wherein the patient suffers from residual symptoms of anxiety or anxiety disorder;

1.29 Any of the foregoing methods, wherein the effective amount is 1 mg-1000 mg, preferably 2.5 mg-50 mg;

1.30 Any of the foregoing methods, wherein the effective amount is 1 mg-100 mg per day, preferably 2.5 mg-50 mg per day;

1.31 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

1.32 Any of the foregoing methods wherein the patient suffers from Parkinson's disease.

Substance-use disorders and substance-induced disorders are the two categories of substance-related disorders defined by the Fifth Edition of the DSM (the Diagnostic and Statistical Manual of Mental Disorders. A substance-use disorder is a pattern of symptoms resulting from use of a substance which the individual continues to take, despite experiencing problems as a result. A substance-induced disorder is a disorder induced by use if the substance. Substance-induced disorders include intoxication, withdrawal, substance induced mental disorders, including substance induced psychosis, substance induced bipolar and related disorders, substance induced depressive disorders, substance induced anxiety disorders, substance induced obsessive-compulsive and related disorders, substance induced sleep disorders, substance induced sexual dysfunctions, substance induced delirium and substance induced neurocognitive disorders.

The DSM-V includes criteria for classifying a substance use disorder as mild, moderate or severe. In some embodiments of the methods disclosed herein, the substance use disorder is selected from a mild substance use disorder, a moderate substance use disorder or a severe substance use disorder. In some embodiments, the substance use disorder is a mild substance use disorder. In some embodiments, the substance use disorder is a moderate substance use disorder. In some embodiments, the substance use disorder is a severe substance use disorder.

Anxiety is a highly prevalent co-morbid disorder in patients undergoing treatment of substance use or substance abuse. A common treatment for substance abuse disorder is the combination of the partial opioid agonist buprenorphine with the opioid antagonist naloxone, but neither of these drugs has any significant effect on anxiety, thus leading to the common result that a third drug, such as a benzodiazepine-class anxiolytic agent. This makes treatment regimens and patient compliance more difficult. In contrast, the Compounds of the present disclosure provide opiate antagonism along with serotonin antagonism and dopamine modulation. This may result in significant enhancement of treatment of patients with substance use or abuse disorder concomitant with anxiety. Depression is also a highly prevalent disorder in patients undergoing substance use or substance abuse treatment. Thus, antidepressants, such as SSRIs, are also often used concomitantly in patients undergoing substance abuse treatment. Compounds of the present disclosure may also enhance treatment in such patients by providing treatment for substance use or substance abuse as well as both anxiety and depression.

The compounds of the present disclosure may have anxiolytic properties ameliorating the need for treatment of a patient with an anxiolytic agent where said patients suffers from co-morbid anxiety. Thus, in some embodiments, the present disclosure provides a method according to Method 1, or any of Methods 1.1-1.32, wherein the central nervous system disorder is a substance addiction, substance use disorders and/or substance-induced disorders, or a substance abuse disorder, for example, in a patient suffering from symptoms of anxiety or who is diagnosed with anxiety as a co-morbid disorder, or as a residual disorder, wherein the method does not comprise the further administration of an anxiolytic agent, such as a benzodiazepine. Benzodiazepines are GABA-modulating compounds, including those discussed with reference to Method 3.1 and 3.2 below.

In another embodiment of the eighth aspect, the present disclosure provides Method 1 or any of Methods 1.1-1.15, wherein the method is further as described as follows:

1.33 Method 1 or any of Methods 1.1-1.32, wherein the central nervous system disorder is a disorder selected from obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, attention deficit-hyperactivity disorder (ADHD), attention deficit disorder (ADD), impulse control disorder, and related disorders, and combination thereof.

1.34 Method 1 or any one Method 1.1-1.33, wherein the central nervous system disorder is selected from obsessive-compulsive disorder (OCD), obsessive-compulsive personality disorder (OCPD), social anxiety disorder, panic disorder, agoraphobia, compulsive gambling disorder, compulsive eating disorder, body dysmorphic disorder and impulse control disorder.

1.35 Method 1 or any one of Method 1.1-1.33, wherein the central nervous system disorder is obsessive-compulsive disorder (OCD) or obsessive-compulsive personality disorder (OCPD).

1.36 Any foregoing method, wherein said patient is not responsive to or cannot tolerate the side effects from, treatment with selective serotonin reuptake inhibitors (SSRIs), such as citalopram, escitalopram, fluoxetine, fluvoxamine, paroxetine, and sertraline.

1.37 Any foregoing method, wherein said patient is not responsive to or cannot tolerate the side effects from, treatment with serotonin-norepinephrine reuptake inhibitors (SNRIs), such as venlafaxine, sibutramine, duloxetine, atomoxetine, desvenlafaxine, milnacipran, and levomilnacipran.

1.38. Any foregoing method, wherein said patient is not response to or cannot tolerate the side effects from, treatment with antipsychotic agents, such as clomipramine, risperidone, quetiapine and olanzapine.

1.39 Method 1 or any of Method 1.1-1.33, wherein the central nervous system disorder is a pain disorder, e.g., a condition associated with pain, such as cephalic pain, idiopathic pain, neuropathic pain, chronic pain (e.g., moderate to moderately severe chronic pain, for example, in patients requiring 24-hour extended treatment for other ailments), fibromyalgia, dental pain, or chronic fatigue.

1.40 Any foregoing method, wherein the patient is not responsive to or cannot tolerate the side effects of non-narcotic analgesics and/or opiate and opioid drugs, or wherein the use of opiate drugs are contraindicated in said patient, for example, due to prior substance abuse or a high potential for substance abuse, such as opiate and opioid drugs including, e.g., morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentantyl, alfentanyl, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, and anileridine, or any combinations thereof;

1.41 Method I or any of Methods 1.1-1.40, wherein the central nervous system disease or disorder is a drug dependency (for example, opiate dependency, cocaine dependency, amphetamine dependency, and/or alcohol dependency), or withdrawal from drug or alcohol dependency (e.g., opiate, cocaine, or amphetamine dependency), and optionally wherein the patient also suffers from a co-morbidity, such as anxiety, depression or psychosis;

1.42 Any of the foregoing methods, wherein the effective amount is 1 mg-1000 mg, preferably 2.5 mg-50 mg;

1.43 Any of the foregoing methods, wherein the effective amount is 1 mg-100 mg per day, preferably 2.5 mg-50 mg per day.

In another embodiment, the present disclosure provides Method 1 or any of Methods 1.1-1.32, or any of Methods 1.33-1.43, wherein the Compounds of Formulas I-IV et seq. or Pharmaceutical Composition 6 or 6.1-6.10 or P.1-P.7 comprises:

1.44 a Compound of Formula II-A, II-B, II-C or II-D, in free or pharmaceutically acceptable salt form, in admixture with a pharmaceutically acceptable diluent or carrier;

1.45 a Compound of Formula III-A, III-B or III-C in free or pharmaceutically acceptable salt form, in admixture with a pharmaceutically acceptable diluent or carrier; or 1.46 a Compound of Formula IV-A, IV-B or IV-C in free or pharmaceutically acceptable salt form, in admixture with a pharmaceutically acceptable diluent or carrier In still another embodiment, the present disclosure provides any of the Methods 1 or 1.1-1.46 as hereinbefore described wherein the disorder is schizophrenia or sleep disorder. In some embodiments, said schizophrenia is associated with depression.

In still another embodiment, the present disclosure provides any of Methods 1.1-1.46, wherein the Depot Composition of the Invention (e.g., Depot Composition of any of formulae 6.8-6.10), or (Pharmaceutical) Composition 6 or 6.1-6.7, or Composition P.1-P.7, is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In still another embodiment, the invention provides any Method 1 or 1.1-1.46 as hereinbefore described, wherein the Depot Composition of the present disclosure is administered for controlled- and/or sustained-release of the Compounds of the Invention over a period of time.

In a ninth aspect, the invention provides a method (Method 2) for the prophylaxis or treatment of one or more sleep disorders comprising administering to a patient in need thereof a Compound of Formulas I-IV et seq. or a Pharmaceutical Composition 6 or 6.1-6.10 or P.1-P.7, (Method 2) for example Method 2 wherein the compound or composition administered is:

2.1 Compound I or 1.1-1.30, in free or pharmaceutically acceptable salt form;

2.2 Compound II or 2.1-2.12, in free or pharmaceutically acceptable salt form;

2.3 Compound III or 3.1-3.11, in free or pharmaceutically acceptable salt form;

2.4 Compound IV or 4.1-4.11, in free or pharmaceutically acceptable salt form;

2.5 Compound 5 or 5.1-5.5;

2.6 Compound of Formula II-A, II-B, II-C or II-D, in free or pharmaceutically acceptable salt form, in admixture with a pharmaceutically acceptable diluent or carrier;

2.7 Compound of Formula III-A, III-B or III-C, in free or pharmaceutically acceptable salt form, in admixture with a pharmaceutically acceptable diluent or carrier;

2.8 Compound of Formula IV-A, IV-B or IV-C, in free or pharmaceutically acceptable salt form, in admixture with a pharmaceutically acceptable diluent or carrier;

2.9 a Pharmaceutical Composition as described by any of Compositions 6 and 6.1-6.10;

2.10 a Pharmaceutical Composition comprising a Compound of Formula II-A, II-B, or II-C, in free or pharmaceutically acceptable salt form, in admixture with a pharmaceutically acceptable diluent or carrier;

2.11 a Pharmaceutical Composition comprising a Compound of Formula III-A, III-B or III-C, in free or pharmaceutically acceptable salt form, in admixture with a pharmaceutically acceptable diluent or carrier;

2.12 a Pharmaceutical Composition comprising a Compound of Formula IV-A, IV-B or IV-C, in free or pharmaceutically acceptable salt form, in admixture with a pharmaceutically acceptable diluent or carrier;

2.13 Depot Composition as described in Depot Composition 6.09 or 6.10;

2.14 Pharmaceutical Composition P.1-P.7;

2.15 Osmotic-controlled Release Oral delivery System Composition as hereinbefore described;

In a further embodiment of the ninth aspect, the invention provides Method 2, or 2.1-2.15, wherein the sleep disorder includes sleep maintenance insomnia, frequent awakenings, and waking up feeling unrefreshed; for example:

2.16 Any of the foregoing methods, wherein the sleep disorder is sleep maintenance insomnia;

2.17 Any of the foregoing methods, wherein the effective amount is 1 mg-5 mg, preferably 2.5-5 mg, per day;

2.18 Any of the foregoing methods, wherein the effective amount is 2.5 mg or 5 mg, per day;

2.19 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;

2.20 Any of the foregoing methods wherein the patient suffers from Parkinson's disease.

In a further embodiment of the ninth aspect, the invention provides Method 2, or any of 2.1-2.20, wherein the sleep disorder includes sleep maintenance insomnia, frequent awakenings, and waking up feeling unrefreshed.

The Compounds of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the present disclosure may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of the present disclosure in combination with one or more second therapeutic agents in free or salt form, wherein the dosages of (i) the second therapeutic agent(s) or (ii) both Compound of the present disclosure and the second therapeutic agents, are lower than if the agents/compounds are administered as a monotherapy. In a particular embodiment, the Compounds of the present disclosure are useful to treat dyskinesia in a patient receiving dopaminergic medications, e.g., selected from levodopa and levodopa adjuncts (carbidopa, COMT inhibitors, MAO-B inhibitors), dopamine agonists, and anti-cholinergics, e.g., such as are used in the treatment of Parkinson's disease.

Therefore, in a tenth aspect, the present disclosure provides Method I, or any of Methods 1.1-35, or Method 2 or any of 2.1-20, further comprising one or more therapeutic agents selected from compounds that modulate GABA activity (e.g., enhances the activity and facilitates GABA transmission), a GABA-B agonist, a 5-HT receptor modulator (e.g., a $5\text{-HT}_{1A}$ agonist, a $5\text{-HT}_{2A}$ antagonist, a $5\text{-HT}_{2A}$ inverse agonist, etc.), a melatonin receptor agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and opiate agonist and/or partial opiate agonist, and an antipsychotic agent, e.g., an atypical antipsychotic agent, in free or pharmaceutically acceptable salt form (Method I-A and II-A respectively; collectively, "Method 3"). In further embodiments of the tenth aspect, the present disclosure provides Method I, or any of Methods 1.1-1.35, or Method 2 or any of 2.1-2.20, further comprising one or more therapeutic agents selected from the foregoing and further selected from agonists or partial agonists of the mu-opiate, kappa-opiate, delta-opiate, and/or nociceptin/orphanin receptors. In further embodiments of the tenth aspect, the present disclosure also provides Method I, or any of Methods 1.1-35, or Method 2 or any of 2.1-2.20, further comprising one or more therapeutic agents selected from a serotonin HT6 receptor antagonist, and an mGluR-2, -3 or -5 receptor agonist or antagonist (including both positive and negative modulators and partial agonists).

In a further embodiment of the tenth aspect, the invention provides Method I-A or II-A as follows, further comprising one or more therapeutic agents.

- 3.1 Method I-A or II-A, wherein the therapeutic agent(s) is compounds that modulate GABA activity (e.g., enhances the activity and facilitates GABA transmission);
- 3.2 Method I-A or II-A or 3.1, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals) and estazolam;
- 3.3 Method I-A or II-A, wherein the therapeutic agent is an additional 5HT2a antagonist;
- 3.4 Method I-A or II-A or 3.3, wherein said additional 5HT2a antagonist is selected from one or more of ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), and AVE8488 (Sanofi-Aventis, France);
- 3.5 Method I-A or II-A, wherein the therapeutic agent is a melatonin receptor agonist;
- 3.6 Method I-A or II-A or 3.5, wherein the melatonin receptor agonist is selected from a group consisting of one or more of melatonin, ramelteon (ROZEREM®, Takeda Pharmaceuticals, Japan), VEC-162 (Vanda Pharmaceuticals, Rockville, Md.), PD-6735 (Phase II Discovery) and agomelatine;

- 3.7 Method I-A or II-A, wherein the therapeutic agent is an ion channel blocker;
- 3.8 Method I-A or II-A or 3.7, wherein said ion channel blocker is one or more of lamotrigine, gabapentin and pregabalin.
- 3.9 Method I-A or II-A, wherein the therapeutic agent is an orexin receptor antagonist;
- 3.10 Method I-A or II-A or 3.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;
- 3.11 Method I-A or II-A, wherein the therapeutic agent is the serotonin-2 antagonist/reuptake inhibitor (SARI);
- 3.12 Method I-A or II-A or 3.11, wherein the serotonin-2 antagonist/reuptake inhibitor (SARI) is selected from a group consisting of one or more Org 50081 (Organon—Netherlands), ritanserin, nefazodone, serzone and trazodone;
- 3.13 Method I-A or II-A, wherein the therapeutic agent is the 5HTIa agonist;
- 3.14 Method I-A or II-A or 3.13, wherein the 5HTIa agonist is selected from a group consisting of one or more of repinotan, sarizotan, eptapirone, buspirone and MN-305 (MediciNova, San Diego, Calif.);
- 3.15 Method I-A or II-A, wherein the therapeutic agent is the neurokinin-1 drug;
- 3.16 Method I-A or II-A or 3.15, wherein the neurokinin-1 drug is Casopitant (GlaxoSmithKline);
- 3.17 Method I-A or II-A, wherein the therapeutic agent is an antipsychotic agent;
- 3.18 Method I-A or II-A or 3.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone and paliperidone;
- 3.19 Method I-A or II-A, wherein the therapeutic agent is an anti-depressant;
- 3.20 Method I-A or II-A or 3.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, and venlafaxine;
- 3.21 Method I-A or II-A, 3.17 or 3.18, wherein the antipsychotic agent is an atypical antipsychotic agent;
- 3.22 Method I-A or II-A, or any of 3.17-3.21, wherein the atypical antipsychotic agent is selected from a group consisting of clozapine, aripiprazole, olanzapine, quetiapine, risperidone, ziprasidone, and paliperidone;
- 3.23 Method I-A or II-A, wherein the therapeutic agent is selected from any of methods 3.1-3.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon—Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone and paliperidone;

3.24 Method I-A or II-A wherein the therapeutic agent is an H3 agonist;

3.25 Method I-A or II-A, wherein the therapeutic agent is an H3 antagonist;

3.26 Method I-A or II-A, wherein the therapeutic agent is a noradrenergic agonist or antagonist;

3.27 Method I-A or II-A, wherein the therapeutic agent is a galanin agonist;

3.28 Method I-A or II-A, wherein the therapeutic agent is a CRH antagonist;

3.29 Method I-A or II-A, wherein the therapeutic agent is a human growth hormone;

3.30 Method I-A or II-A, wherein the therapeutic agent is a growth hormone agonist;

3.31 Method I-A or II-A, wherein the therapeutic agent is estrogen;

3.32 Method I-A or II-A, wherein the therapeutic agent is an estrogen agonist;

3.33 Method I-A or II-A, wherein the therapeutic agent is a neurokinin-1 drug;

3.34 Method I-A or II-A, wherein a therapeutic agent is combined with compounds of Formula (I) and the therapeutic agent is an anti-Parkinson agent such as L-dopa, co-careldopa, duodopa, stalevo, Symmetrel, benztropine, biperiden, bromocriptine, entacapone, pergolide, pramipexole, procyclidine, ropinirole, selegiline and tolcapone;

3.35 Method I-A or II-A, wherein the therapeutic agent is an opiate agonist or partial opiate agonist, for example, a mu-agonist or partial agonist, or a kappa-agonist or partial agonist, including mixed agonist/antagonists (e.g., an agent with partial mu-agonist activity and kappa-antagonist activity);

3.36 Method 3.35, wherein the therapeutic agent is buprenorphine, optionally, wherein said method does not include co-treatment with an anxiolytic agent, e.g., a GABA compound or benzodiazepine;

3.37 Method I-A or II-A, wherein compounds of Formula (I) may be used to treat sleep disorders, depression, psychosis, or any combinations thereof, in patients suffering from the listed diseases and/or Parkinson's disease;

3.38 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

3.39 Any of the foregoing methods wherein the disorder is sleep disorder;

3.40 Any of the foregoing methods, wherein the disorder is sleep disorder associated with psychosis, e.g., schizophrenia or Parkinson's disease; in free or pharmaceutically acceptable salt form.

In an eleventh aspect of the invention, the combination of a Compound of the present disclosure and one or more second therapeutic agents as described in Methods I-A, II-A or any of Methods 3 or 3.1-3.40 may be administered as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods I-A, II-A, 3 or 3.1-3.40 comprises administering to a patient in need thereof, a Compound of the Invention in combination with an atypical antipsychotic agent, e.g., a compound selected from clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods I-A, II-A, 3 or 3.1-3.40 comprises administering to a patient in need thereof, a Compound of the Invention in combination with an anti-depressant, e.g., amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compound of the Invention.

In still another embodiment, Methods I-A, II-A, 3 or 3.1-3.40 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam or any combinations thereof, in free or pharmaceutically acceptable salt form. In other embodiments, the methods disclosed herein do not further comprise administration of an GABA compound, a benzodiazepine or any other anxiolytic agent.

In another preferred embodiment, Methods I-A, II-A, 3 or 3.1-3.40 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods I-A, II-A, 3 or 3.1-3.40 comprises administering to a patient in need thereof, a Compound of the Invention in combination (including as part of a daily dosage regimen) with an atypical stimulant, e.g., a modafinil, adrafinil, or armodafinil. A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In some embodiments of each of the Compounds of Formulas I-IV et seq.; Pharmaceutical Compositions 6 and 6.1-6.8; Depo Compositions 6.9 and 6.10; Compositions P.1-P.7; Methods 1 and 1.1-1.46; and Methods 2 and 2.1-2.20; the compound of the present disclosure is substantially free of compound of Formula A.

In a twelfth aspect, the invention provides use of a compound as described in the following:

11.1 Compound I or 1.1-1.30, in free or pharmaceutically acceptable salt form;

11.2 Compound II or 2.1-2.12, in free or pharmaceutically acceptable salt form;

11.3 Compound III or 3.1-3.11, in free or pharmaceutically acceptable salt form;

11.4 Compound IV or 4.1-4.11, in free or pharmaceutically acceptable salt form;

11.5 Compound 5 or 5.1-5.5;

11.6 a Compound of Formula II-A, II-B, II-C, II-D, or II-E in free or pharmaceutically acceptable salt form;

11.7 a Compound of Formula III-A, III-B or III-C, in free or pharmaceutically acceptable salt form;

11.8 a Compound of Formula IV-A, IV-B or IV-C, in free or pharmaceutically acceptable salt form;

11.9 Pharmaceutical Composition 6 and 6.1-6.10;

11.10 Pharmaceutical Composition P.1-P.7;

11.11 Osmotic-controlled Release Oral delivery System Composition as hereinbefore described;

(in the manufacture of a medicament) for the treatment or prophylaxis of one or more disorders as disclosed hereinbefore, e.g., in any of Method 1 or 1.1-1.46, any of Method 2 and 2.1-2.20, and Method 3 or 3.3-3.40, or any methods described in the eleventh aspect of the invention.

In the thirteenth aspect, the invention provides a pharmaceutical composition as hereinbefore described, e.g.:

12.1 Pharmaceutical Composition 6 and 6.1-6.10;

12.2 Pharmaceutical Composition P.1-P.7;

12.3 Osmotic-controlled Release Oral delivery System Composition as hereinbefore described, for use in the treatment or prophylaxis of one or more disorders as disclosed hereinbefore, e.g., in any of Methods 1 and 1.1-1.46, Methods 2 and 2.1-2.20, Methods I-A, II-A, 3 or 3.1-3.40 or any methods described in the eleventh or twelfth aspect of the invention.

DETAILED DESCRIPTION OF THE INVENTION

Figure 1:
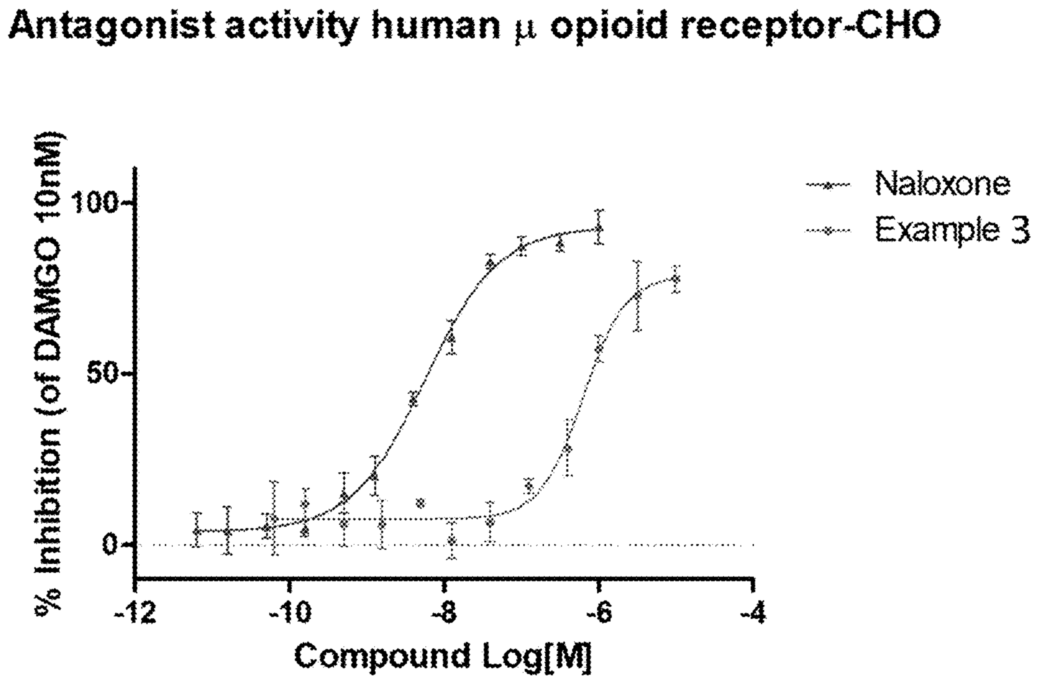
FIG. 1 shows the mu-receptor antagonist activity of the compound of Example 3 compared to naloxone, as described in Example 10.

If not otherwise specified or clear from context, the following terms as used herein have the following meetings:

"Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example in some embodiments wherein $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The term "pharmaceutically acceptable diluent or carrier" is intended to mean diluents and carriers that are useful in pharmaceutical preparations, and that are free of substances that are allergenic, pyrogenic or pathogenic, and that are known to potentially cause or promote illness. Pharmaceutically acceptable diluents or carriers thus exclude bodily fluids such as example blood, urine, spinal fluid, saliva, and the like, as well as their constituent components such as blood cells and circulating proteins. Suitable pharmaceutically acceptable diluents and carriers can be found in any of several well-known treatises on pharmaceutical formulations, for example Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; and Martindale, The Extra Pharmacopoeia, Thirty-Second Edition (The Pharmaceutical Press, London, 1999); all of which are incorporated by reference herein in their entirety.

The terms "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization, LC-MS and LC-MS/MS techniques and the like), in sufficient purity to be characterizable by standard analytical techniques described herein or well known to the skilled artisan.

The Compounds of Formula I, wherein Z is —(C═O)— or —(CH(OH))—, including for example the Compounds of Formulae II-B and II-C, may be produced as metabolites of a compound of Formula A, and/or as metabolites of a compound of Formula B:

Formula A

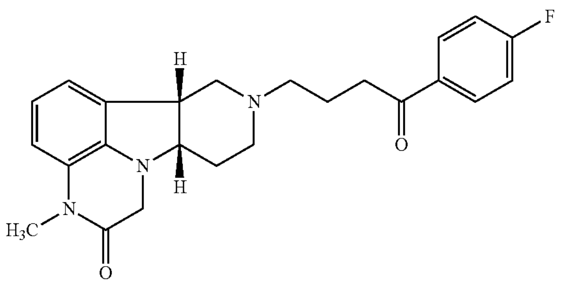

Formula B

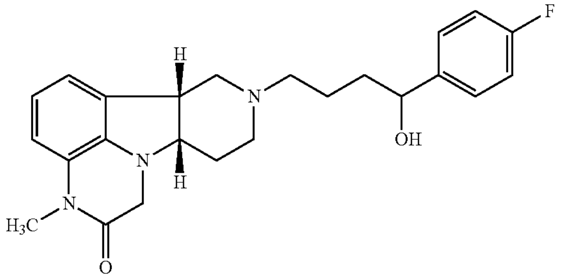

The compound of Formula A is known to provide effective treatment of 5-$HT_{2A}$, SERT and/or $D_2$ receptor related disorders without significant extrapyramidal side effects, as similarly disclosed and claimed in WO 2009/145900, the contents of which are incorporated by reference in their entirety. The plasma levels of compounds of Formulas II-B and II-C produced from metabolism of a compound of Formula A are, however, quite low and probably do not contribute significantly to the therapeutic activity of the compound of Formula A. Compounds of Formulae II-D and II-E could also be present as metabolites, although this has so far not been detected. The Compounds of Formula I have unexpectedly been found to have activity as antagonists of the μ-opioid receptor. This is unexpected because the compound of Formula A has not been know or understood to have any μ-opioid receptor activity or binding. Compounds of Formula I wherein X is —NH— and wherein L is —O— are shown to have particularly good μ-opioid receptor antagonism. Such Compounds of Formula I may therefore be useful in the treatment of drug dependency, such as opiate dependency and/or alcohol dependency, by inhibiting the endogenous opiate response to illicit drug administration, as well as by inhibiting the direct effects of ingestion of illicit opiate drugs.

It is surprising that metabolites of a compound of Formula A have somewhat different relative receptor binding affinity that compounds of Formula A. For example, the receptor binding profile of the compound for Formula II-B is very unique, with a combination of antagonist activities at 5-$HT_{2A}$, $D_1$ and Mu opiate receptors, making this compound very interesting for treating mood disorders. The compound of Formula A is not active at the Mu opiate receptor, for example.

Unless otherwise indicated, the Compounds of the present disclosure, e.g., Compound I or 1.1-1.30, Compound II or 2.1-2.18, Compound III or 3.1-3.13, or Compound IV or 4.1-4.13 (collectively, Compounds of Formulas I-IV et seq.) may exist in free or salt, e.g., as acid addition salts, form. An acid-addition salt of a compound of the invention which is sufficiently basic, for example, an acid-addition salt with, for example, an inorganic or organic acid, for example hydrochloric, hydrobromic, sulphuric, phosphoric, acid acetic, trifluoroacetic, citric, maleic acid, toluene sulfonic, propionic, succinic, glycolic, stearic, lactic, malic, tartaric, citric, ascorbic, pamoic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. In addition a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)-amine. In a particular embodiment, the salt of the Compounds of the Invention is a toluenesulfonic acid addition salt. In another particular embodiment, the salt of the Compounds of the Invention is a fumaric acid addition salt. In a particular embodiment, the salt of the Compounds of the Invention is a phosphoric acid addition salt.

The Compounds of the present disclosure are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included.

The Compounds of the present disclosure may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

It is also intended that the compounds of the present disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the compounds of the disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention. In addition, the substitution of atoms of having the natural isotopic distributing with heavier isotopes can result in desirable change in pharmacokinetic rates when these substitutions are made at metabolically liable sites. For example, the incorporation of deuterium ($^2H$) in place of hydrogen can slow metabolic degradation when the position of the hydrogen is a site of enzymatic or metabolic activity.

In addition to the unique characteristic of the Compounds of the present disclosure, the Compounds of Formula I, wherein Y is —C(H)(OH)— may also be esterified to form physiologically hydrolysable and acceptable ester prodrugs. As used herein, "physiologically hydrolysable and acceptable esters" means esters of Compounds of the present disclosure which are hydrolysable under physiological conditions to yield hydroxy on the one hand and acid, e.g., carboxylic acid on the other, which are themselves physiologically tolerable at doses to be administered. For Example, the Compound of Formula I or Formula II wherein Y is —C(H)(OH) may be esterified to form a prodrug, i.e., a Compound of Formula I Formula II wherein $R_1$ is —C(O)—$C_{1-21}$ alkyl. In some preferred embodiments, $R_1$ is —C(O)—$C_{1-21}$alkyl, e.g., acyl acid esters, e.g., heptanoic, octanoic, decanoic, dodecanoic, tetradecanoic or hexadecanoic acid ester.

Similarly, wherein the Compounds of the present disclosure contain an amine group, prodrug of such amine, e.g., methyl amine prodrugs may also exist wherein the prodrug is cleaved to release the amine metabolite in vivo following administration.

The prodrugs of the Compounds of the present disclosure wherein $R_1$ is —C(O)—$C_{1-21}$alkyl, preferably —$C_{6-21}$alkyl, more preferably $C_{6-15}$alkyl, more preferably linear, saturated or unsaturated and optionally substituted with one or more hydroxy or alkoxy groups, are particularly useful for sustained- and/or delayed release so as to achieve a long acting effect, e.g., wherein the Compounds of the present disclosure is released over a period of from about 14 to about 30 to about 180 days, preferably over about 30 or about 60 or about 90 days, for example as described in any of depot composition as described herein. Preferably, the sustained and/or delayed-release formulation is an injectable formulation.

Alternatively and/or additionally, the Compounds of the present disclosure may be included as a depot formulation, e.g., by dispersing, dissolving or encapsulating the Compounds of the Invention in a polymeric matrix as described in any of Composition 6 and 6.1-6.10, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d,l-lactide-co-glycolide) have a central glucose moiety having rays of linear polylactide chains.

The depot compositions of the invention (e.g., Compositions 6 and 6.1-6.10, in a polymer matrix) as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. No. 4,389,330 and U.S. Pat. No. 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the present disclosure incorporated in the microparticles usually ranges from about 1 wt % to about 90 wt. %, preferably 30 to 50 wt. %, more preferably 35 to 40 wt. %. By weight % is meant parts of the Compounds of the present disclosure per total weight of microparticle.

The pharmaceutical depot compositions may comprise a pharmaceutically-acceptable diluent or carrier, such as a water miscible diluent or carrier.

Details of Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, parenterally (intravenously, intramuscular or subcutaneous) or transdermally, but are preferably administered orally. In certain embodiment, the Compounds of the Invention, e.g., in depot formulation, is preferably administered parenterally, e.g., by injection.

In general, satisfactory results for Method 1 and 1.1-1.46, Method 2 and 2.1-2.20, and Method 3 and 3.1-3.40, or use of the Compounds of the present disclosure as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; (4) sleep disorders associated with psychosis, e.g., schizophrenia, or Parkinson's disease; and (5) substance addiction, substance use disorders and/or substance-induced disorders, as set forth above are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration.

Satisfactory results for Method 2 or 2.1-2.20 or use of the Compounds of the present disclosure as hereinbefore described, e.g. for the treatment of sleep disorder alone are indicated to be obtained on oral administration at dosages of the order from about 2.5 mg-5 mg, e.g., 2.5 mg, 3 mg, 4 mg or 5 mg, of a Compound of the Invention, in free or pharmaceutically acceptable salt form, once daily, preferably via oral administration.

Satisfactory results for Method I-A or Method II-A, or any of 3.1-3.40 are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 3.1-3.40 are indicated to be obtained at less than 5 mg, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. Duration of action of the Compounds of the present disclosure may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the present disclosure can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Pharmaceutical compositions comprising Compounds of the present disclosure may be prepared using conventional diluents or excipients (an example include, but is not limited to sesame oil) and techniques known in the galenic art. Thus oral dosage forms may include tablets, capsules, solutions, suspensions and the like.

Methods of Making the Compounds of the Invention:

The Compounds of the present disclosure wherein X is —NH— or —$N(CH_3)$— and Y is —C(=O) may be prepared by reacting (6bR, 10aS)-2-oxo-2,3,6b,9,10,10a-hexahydro-1H,7H-pyrido[3',4':4,5]pyrrolo[1,2,3-de]quinoxaline or its 1-methyl analog with 4-chloro-4'-fluorobutyrophenone, in accordance with Scheme 1 below:

Scheme 1

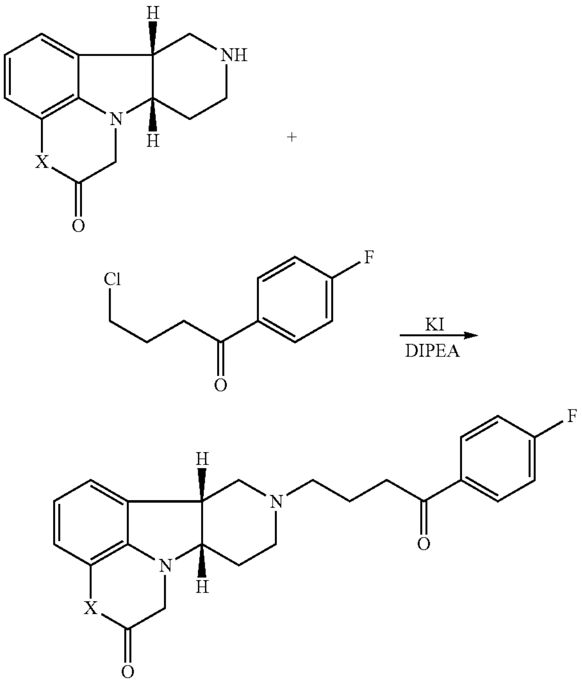

X = —NH— or —$N(CH_3)$—

Compounds of the present disclosure wherein X is —NH— or —$N(CH_3)$— and Y is —CH(OH)— may be prepared by reacting the 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one produced in Scheme 1 (or its 1-methyl analog) with a reducing agent, in accordance with Scheme 2, below:

Scheme 2

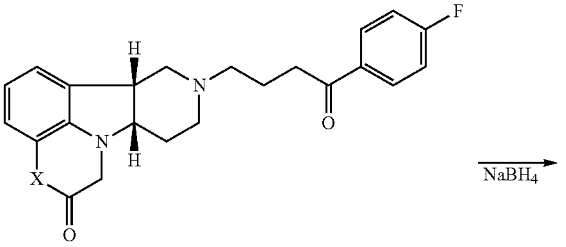

-continued

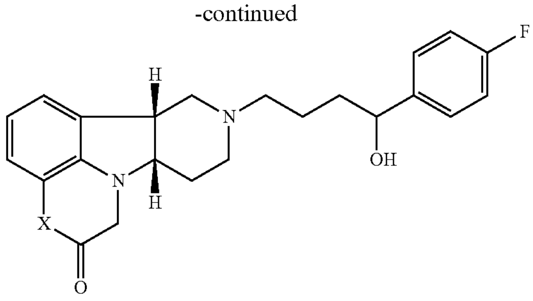

X = —NH— or —N($CH_3$)—

The reducing agent may be a metal hydride, e.g., sodium borohydride, sodium cyanoborohydride, lithium aluminum hydride, aluminum hydride, diisobutylaluminum hydride, preferably sodium borohydride. Further reagents for reduction of ketones may be found in Jerry March, Advanced Organic Chemistry, Reactions Mechanisms and Structures, p. 910-911, (1992, John Wiley & Sons, Inc.), Fourth Edition, the contents of which are incorporated by reference.

(a) L-C(O)—$C_{1-21}$alkyl, wherein L is a leaving group such as a halo group (for example, chloro or bromo), trifluoromethylsulfonyloxy (—$OSO_2CF_3$), tosyloxy (—O—$S(O)_2$—$C_6H_4$—$CH_3$), methylsulfonyloxy (—O—$S(O)_2$—$CH_3$), 1H-benzo[d][1,2,3]triazol-1-yloxy or succinimidyloxy group, with (b) the Compound of Formula I wherein Y is —C(H)(OH), preferably in the presence of a base (e.g., diisopropylamine, triethyl amine or pyridine). For example L-C(O)—$C_{1-21}$alkyl is an acetyl halide, decanoyl halide or heptanoyl halide, which may be prepared by reacting HO—C(O)—$C_{1-2}$alkyl, e.g., with thionyl chloride, $P(X')_3$ or $P(X')_5$ wherein X' is Cl or Br. Wherein L is tosyloxy-C(O)—$C_{1-21}$alkyl or methylsulfonyloxy-C(O)—$C_{1-21}$alkyl, these compounds may be prepared by reacting HO—C(O)—$C_{1-21}$alkyl with tosyl-chloride or mesyl-chloride, preferably in the presence of a base such as pyridine. Synthesis of the Compound of Formula II-A where $R_1$ is other than H may be summarized in Scheme 3 below:

Scheme 3

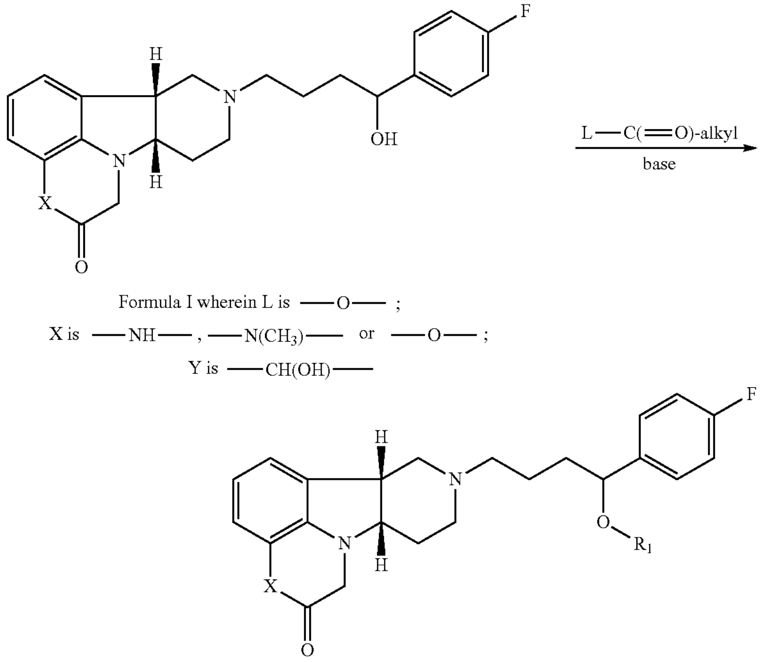

Formula II-A
$R_1$ is C(=O)-alkyl

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

The Compounds of Formula I wherein Y is —CH(O—$R_1$)— and $R_1$ is other than H can be prepared by several commonly used esterification methods such as alcoholysis of acyl halides, anhydrides or active esters. For example, The Compound of Formula I, wherein $R_1$ is —C(O)— alkyl may be prepared by reacting:

Alternatively, the synthesis of the compound of Formula II-A where $R_1$ is other than H maybe achieved by reacting HO—C(O)—$C_{1-21}$alkyl with (i) a compound of Formula I wherein Y is —C(H)(OH) in the presence of a base such as DIEPA and $NEt_3$, and (ii) a dehydrating or coupling reagent such as 2-fluoro-1-ethyl pyridinium tetrafluoroborate (FEP), tetramethylfluoromamidinium hexafluorophosphate (TFFH) or 1,1,3,3-bis(tetramethylene) chlorouronium hexafluorophosphate (PyClU).

Salts of the Compounds of the present disclosure may be prepared as similarly described in U.S. Pat. Nos. 6,548,493; 7,238,690; 6,552,017; 6,713,471; 7,183,282; U.S. RE39680;

U.S. RE39679; and WO 2009/114181, the contents of each of which are incorporated by reference in their entirety.

Diastereomers of prepared compounds can be separated by, for example, HPLC using CHIRALPAK® AY-H, 5μ, 30×250 mm at room temperature and eluted with 10% ethanol/90% hexane/0.1% dimethylethylamine. Peaks can be detected at 230 nm to produce 98-99.9% ee of the diastereomer.

Example 1: Synthesis of 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one

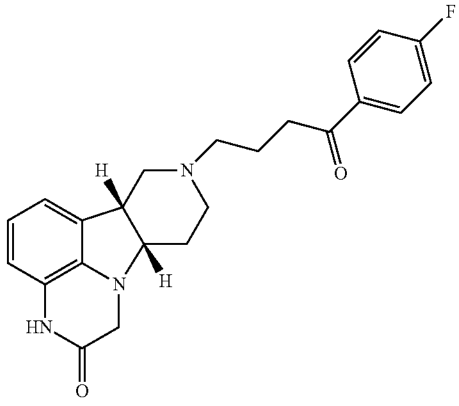 [SMILES: O=C1CN2c3c(cccc3[C@@H]3CN(CCCC(=O)c4ccc(F)cc4)CC[C@@H]32)N1]

(6bR, 10aS)-2-oxo-2,3,6b,9,10,10a-hexahydro-1H,7H-pyrido[3',4':4,5]pyrrolo[1,2,3-de]quinoxaline-8-carboxylic acid ethyl ester (6.4 g, 21.2 mmol) is suspended in HBr acetic acid solution (64 mL, 33% w/w) at room temperature. The mixture is heated at 50° C. for 16 h. After cooling, and treatment with ethyl acetate (300 mL), the mixture is filtered. The filter cake is washed with ethyl acetate (300 mL), and then dried under vacuum. The obtained HBr salt is then suspended in methanol (200 mL), and cooled with dry ice in isopropanol. Under vigorous stirring, ammonia solution (10 mL, 7N in methanol) is added slowly to the suspension to adjust the pH of the mixture to 10. The obtained mixture is dried under vacuum without further purification to give crude (6bR, 10aS)-2-oxo-2,3,6b,9,10,10a-hexahydro-1H,7H-pyrido[3',4':4,5]pyrrolo[1,2,3-de]quinoxaline (8.0 g), which is used directly in the next step. MS (ESI) m/z 230.2 $[M+H]^+$.

The crude (6bR, 10aS)-2-oxo-2,3,6b,9,10,10a-hexahydro-1H,7H-pyrido[3',4':4,5]pyrrolo[1,2,3-de]quinoxaline (1.4 g) is dissolved in DMF (14 mL), and then KI (2.15 g) and 4-Chloro-4'-fluorobutyrophenone (2 mL) are added successively. The mixture is degassed with argon, followed by adding N,N-diisopropylethylamine (DIPEA, 2 mL). The mixture is heated at 78° C. for 2 h. After cooling, the solvents are removed under reduced pressure. The dark brown residue is suspended in dichloromethane (100 mL) and then extracted with water (30 mL). The organic layer is separated, and dried over $K_2CO_3$. After filtration, the solvents are removed under reduced pressure. The obtained crude product is purified by silica gel column chromatography eluting with 0-10% of methanol in ethyl acetate containing 0.1% of 7N ammonia in methanol to yield 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one as a light yellow solid (767 mg). $^1$H NMR (500 MHz, DMSO-$d_6$) δ 10.3 (s, 1H), 8.1-8.0 (m, 2H), 7.3 (dd, J=8.86 Hz, 2H), 6.8 (d, J=7.25 Hz, 1H), 6.6 (dd, J=7.55 Hz, 1H), 6.6 (d, J=7.74 Hz, 1H), 3.8 (d, J=14.49 Hz, 1H), 3.3-3.3 (m, 1H), 3.2-3.2 (m, 1H), 3.1-3.0 (m, 1H), 3.0 (t, J=6.88 Hz, 2H), 2.8-2.8 (m, 1H), 2.6-2.5 (m, 1H), 2.3-2.2 (m, 2H), 2.1-2.0 (m, 1H), 1.9-1.8 (m, 1H), 1.8 (t, J=6.99 Hz, 2H), 1.6 (t, J=11.25 Hz, 2H). MS (ESI) m/z 394.2 $[M+H]^+$.

Example 2: Synthesis of 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-ol

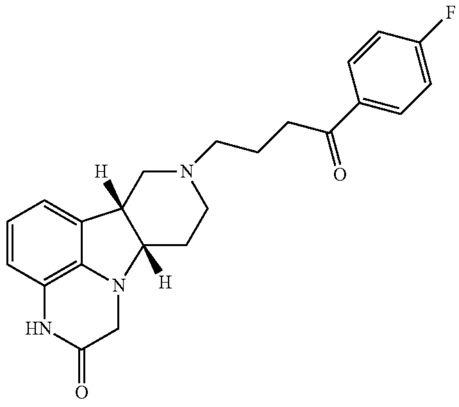 [SMILES: O=C1CN2c3c(cccc3[C@@H]3CN(CCCC(=O)c4ccc(F)cc4)CC[C@@H]32)N1]

4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-one (50 mg, 0.127 mmol) is dissolved in methanol (5 mL). Under stirring, $NaBH_4$ (31 mg, 0.82 mmol) is added in batches. After the completion of the addition, the mixture is stirred at room temperature for 30 min. Methanol is evaporated under reduced pressure. The residue is dissolved in dichloromethane (10 mL) and then extracted with water (2×0.5 mL). The combined organic phase is dried over $K_2CO_3$. After filtration, the filtrate is concentrated under reduced pressure and then further dried under vacuum to give 4-((6bR,10aS)-2-oxo-2,3,6b,9,10,10a-hexahydro-1H,7H-pyrido[3',4':4,5]pyrrolo[1,2,3-de]quinoxalin-8-yl)-1-(4-fluoro-phenyl)-butan-1-ol as a pale yellow foamy solid (45 mg, yield 90%). $^1$H NMR (500 MHz, DMSO-$d_6$) δ 10.3 (s, 1H), 7.4-7.3 (m, 2H), 7.2-7.1 (m, 2H), 6.7 (d, J=7.29 Hz, 1H), 6.7-6.6 (m, 1H), 6.6 (d, J=7.74 Hz, 1H), 5.4 (s, 1H), 4.7-4.4 (m, 1H), 3.8 (d, J=14.49 Hz, 1H), 3.3-3.3 (m, 1H), 3.3-3.2 (m, 1H), 3.2-3.1 (m, 1H), 2.8-2.7 (m, 1H), 2.6-2.5 (m, 1H), 2.3-2.1 (m, 2H), 2.1-2.0 (m, 1H), 2.0-1.9 (m, 1H), 1.8-1.7 (m, 1H), 1.7-1.5 (m, 3H), 1.5-1.4 (m, 1H), 1.4-1.3 (m, 1H). MS (ESI) m/z 396.2 $[M+H]^+$.

Example 3: Synthesis of (6bR,10aS)-8-(3-(4-fluorophenoxy)propyl)-6b,7,8,9,10,10a-hexahydro-1H-pyrido[3',4':4,5]pyrrolo[1,2,3-de]quinoxalin-2(3H)-one

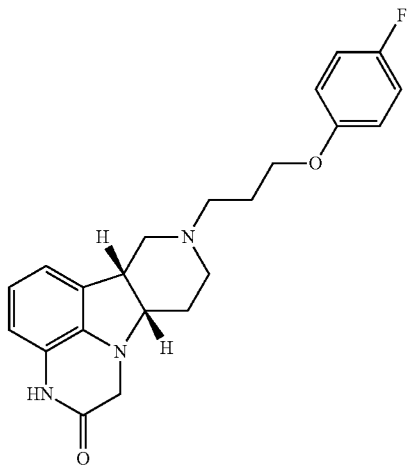 [SMILES: O=C1CN2c3c(cccc3[C@@H]3CN(CCCOc4ccc(F)cc4)CC[C@@H]32)N1]

A mixture of (6bR,10aS)-6b,7,8,9,10,10a-hexahydro-1H-pyrido[3',4':4,5]pyrrolo[1,2,3-de]quinoxalin-2(3H)-one (100 mg, 0.436 mmol), 1-(3-chloroproxy)-4-fluorobenzene (100 μL, 0.65 mmol) and KI (144 mg, 0.87 mmol) in DMF (2 mL) is degassed with argon for 3 minutes and DIPEA (150 μL, 0.87 mmol) is added. The resulting mixture is heated to 78° C. and stirred at this temperature for 2 h. The mixture is cooled to room temperature and then filtered. The filter cake is purified by silica gel column chromatography using a gradient of 0-100% ethyl acetate in a mixture of methanol/7N $NH_3$ in methanol (1:0.1 v/v) as an eluent to produce partially purified product, which is further purified with a semi-preparative HPLC system using a gradient of 0-60% acetonitrile in water containing 0.1% formic acid over 16 min to obtain the title product as a solid (50 mg, yield 30%). MS (ESI) m/z 406.2 $[M+1]^+$. $^1H$ NMR (500 MHz, DMSO-$d_6$) δ 10.3 (s, 1H), 7.2-7.1 (m, 2H), 7.0-6.9 (m, 2H), 6.8 (dd, J=1.03, 7.25 Hz, 1H), 6.6 (t, J=7.55 Hz, 1H), 6.6 (dd, J=1.07, 7.79 Hz, 1H), 4.0 (t, J=6.35 Hz, 2H), 3.8 (d, J=14.74 Hz, 1H), 3.3-3.2 (m, 3H), 2.9 (dd, J=6.35, 11.13 Hz, 1H), 2.7-2.6 (m, 1H), 2.5-2.3 (m, 2H), 2.1 (t, J=11.66 Hz, 1H), 2.0 (d, J=14.50 Hz, 1H), 1.9-1.8 (m, 3H), 1.7 (t, J=11.04 Hz, 1H).

Example 4: Cellular and Nuclear Receptor Functional Assays

Cellular and Nuclear Receptor Functional Assays are performed on the compounds of Formula II-B and II-C according to the procedure of Wang, J. B. et al. (1994), *FEBS Lett.,* 338:217-222. The compounds are tested at several concentrations to determine their $IC_{50}$ or $EC_{50}$. Cellular agonist effects are calculated as percent of control response to a known reference agonist for each target and cellular antagonist effect is calculated as a percent inhibition of control reference agonist response for each target.

The following assay is performed to determine the effect of the Compound of Formula II-B on the μ (MOP) (h) receptor:

| Assay (Receptor) | Source | Stimulus | Incubation | Measured Component | Detection Method |
|---|---|---|---|---|---|
| μ (MOP) (h) (agonist effect) | human recombinant (CHO cells) | none (0.3 μM DAMGO for control) | 10 min @ 37° C. | cAMP | HTRF |
| μ (MOP) (h) (antagonist effect) | human recombinant (CHO cells) | DAMGO (20 nM) | 10 min @ 37° C. | cAMP | HTRF |

For the antagonists, the apparent dissociation constants ($K_B$) are calculated using the modified Cheng Prusoff equation:

$$K_B = \frac{IC_{50}}{1 + (A / EC_{50A})}$$

where A=concentration of reference agonist in the assay, and $EC_{50A}$=$EC_{50}$ value of the reference agonist.

The compound of Formula II-B is found to have a μ (MOP) (h) (antagonist effect) with an $IC_{50}$ of $1.3\times10^{-6}$M; and a $K_B$ of $1.4\times10^{-7}$M; and the compound of Formula II-C is found to have an $IC_{50}$ greater than $1\times10^{-5}$, which was the highest concentration tested.

The results are expressed as a percent of control agonist response:

$$\frac{\text{measured response}}{\text{control response}} \times 100$$

and as a percent inhibition of control agonist response:

$$100-\left(\frac{\text{measured response}}{\text{control response}}\times 100\right)$$

obtained in the presence of the Compound of Formula II-B or II-C.

The $EC_{50}$ values (concentration producing a half-maximal response) and $IC_{50}$ values (concentration causing a half-maximal inhibition of the control agonist response) are determined by non-linear regression analysis of the concentration-response curves generated with mean replicate values using Hill equation curve fitting:

$$Y = D + \left[\frac{A-D}{1+(C/C_{50})^{nH}}\right]$$

where Y=response, A=left asymptote of the curve, D=right asymptote of the curve, C=compound concentration, and $C_{50}$=$EC_{50}$ or $IC_{50}$, and nH=slope factor. The analysis is performed using software developed in-house and validated by comparison with data generated by the commercial software SigmaPlot® 4.0 for Windows® (© 1997 by SPSS Inc.).

Example 5: Receptor Binding Profile of Compound of Formulas II-B and II-C

Receptor binding is determined for the Compounds of Formulas II-A and II-B using the tosylate salt of the compound of Formula A as a control. The following literature procedures are used, each of which reference is incorporated herein by reference in their entireties: $5\text{-}HT_{2A}$: Bryant, H. U. et al. (1996), *Life Sci.,* 15:1259-1268; D2: Hall, D. A. and Strange, P. G. (1997), *Brit. J. Pharmacol.,* 121:731-736; D1: Zhou, Q. Y. et al. (1990), *Nature,* 347:76-80; SERT: Park, Y. M. et al. (1999), *Anal. Biochem.,* 269:94-104; Mu opiate receptor: Wang, J. B. et al. (1994), *FEBS Lett.,* 338:217-222.

In general, the results are expressed as a percent of control specific binding:

$$\frac{\text{measured specific binding}}{\text{control specific binding}}\times 100$$

and as a percent inhibition of control specific binding:

$$100-\left(\frac{\text{measured specific binding}}{\text{control specific binding}}\times 100\right)$$

obtained in the presence of the test compounds.

The $IC_{50}$ values (concentration causing a half-maximal inhibition of control specific binding) and Hill coefficients (nH) are determined by non-linear regression analysis of the competition curves generated with mean replicate values using Hill equation curve fitting:

$$Y = D + \left[\frac{A-D}{1+(C/C_{50})^{nH}}\right]$$

where Y=specific binding, A=left asymptote of the curve, D=right asymptote of the curve, C=compound concentration, $C_{50}$=$IC_{50}$, and nH=slope factor. This analysis was performed using in-house software and validated by comparison with data generated by the commercial software SigmaPlot® 4.0 for Windows® (© 1997 by SPSS Inc.). The inhibition constants (Ki) were calculated using the Cheng Prusoff equation:

$$Ki = \frac{IC_{50}}{(1 + L/K_D)}$$

where L=concentration of radioligand in the assay, and $K_D$=affinity of the radioligand for the receptor. A Scatchard plot is used to determine the $K_D$.

The following receptor affinity results are obtained, using the tosylate salt of a Compound of Formula A as a control:

| Receptor | Formula II-B (Ex. 1) | Formula II-C (Ex. 2) | Example 3 | Formula A (tosylate salt) |
|---|---|---|---|---|
| | Ki (nM) or maximum inhibition | | | |
| $5\text{-}HT_{2A}$ | 11 | 31% inhibition at 240 nM | 8.3 | 10 |
| D2 | 47% inhibition at 240 nM | 11% inhibition at 240 nM | 160 | 49 |
| D1 | 22 | 13% inhibition at 100 nM | 50 | 41 |
| SERT | 44% inhibition at 240 nM | No inhibition seen | 590 | 16 |
| Mu opiate receptor | 22 | 85 | 11 | >10,000 |

Example 6: DOI-Induced Head Twitch Model in Mice

R-(−)-2,5-dimethoxy-4-iodoamphetamine (DOI) is an agonist of the serotonin $5\text{-}HT_2$ receptor family. When administered to mice, it produces a behavioral profile associated with frequent head twitches. The frequency of these head twitches during a predetermined period of time can be taken as an estimate of $5\text{-}HT_2$ receptor agonism in the brain. Conversely, this behavioral assay can be used to determine $5\text{-}HT_2$ receptor antagonism in the brain by administering the DOI with or without an antagonist and recording the reduction in DOI-induced head twitches after the administration of the antagonist.

The method of Darmani et al., *Pharmacol Biochem Behav.* (1990) 36:901-906 (the contents of which are incorporated by reference in their entirety) is used with some modifications. (±)-DOI HCl is injected subcutaneously and the mice are immediately placed in a conventional plastic cage. The number of head twitches is counted during 6 min, beginning 1 min after DOI administration. The tested compound is administered orally 0.5 hr before the injection of DOI. Results area calculated as the $EC_{50}$ for reducing DOI-induced head twitches. The results are shown in the following Table:

| Compound | $EC_{50}$ (mg/kg, p.o.) |
|---|---|
| Example 1 (Formula II-B) | 0.23 |
| Example 2 (Formula II-C) | 2.03 |
| Example 3 | 0.44 |
| Formula A | 0.09 |
| Formula B | 0.31 |

The results show that the compounds of Example 1 and 3 potently block DOI head twitch, comparable to the reference compounds Formula A and C, and consistent with the in-vitro 5-$HT_{2A}$ results shown in Example 5. In contrast, the compound of Example 2 is relatively inactive in this functional assay, confirming that this compound is relatively weaker in its serotonin receptor antagonism than other structurally similar compounds.

Example 7: Mouse Tail Flick Assay

The Mouse Tail Flick Assay is a measure of an analgesia, indicated by the pain reflex threshold of restrained mice. Male CD-1 mice are positioned with their tails under a focused beam of high-intensity infrared heat source, resulting in heating of the tail. The amount of time (latency) between turning on heating instrument and the flicking of the mouse's tail out of path of the heat source is recorded. Administration of morphine results in analgesia, and this produces a delay in the mouse's reaction to the heat (increased latency). Prior administration of a morphine antagonist, i.e., naloxone, reverses the effect and results in normal latency time. This test is used as a functional assay to gauge antagonism of mu-opiate receptors.

Ten male CD-1 mice (about 8 weeks of age) are assigned to each of five treatment groups. The groups are treated as follows: Group (1) [negative control]: administered 0.25% methylcellulose vehicle p.o., 60 minutes before the tail flick test, and saline vehicle 30 minutes before the tail flick test; Group (2) [positive control]: administered 0.25% methylcellulose vehicle p.o., 60 minutes before the test, and 5 mg/kg morphine in saline 30 minutes before the test; Group (3) [positive control]: administered 3 mg/kg naloxone in saline 50 minutes before the test, and 5 mg/kg morphine in saline 30 minutes before the test; Groups (4)-(6): administered either 0.1 mg/kg, 0.3 mg/kg or 1 mg/kg of the test compound in 0.25% methylcellulose vehicle p.o., 60 minutes before the test, and 5 mg/kg morphine in 30 minutes before the test. The experiment is repeated for the compounds of Example 1 and Example 3. The results are shown in the following table as mean latency measured in seconds:

| | Group 1 Veh/Veh | Group 2 Veh/Mor | Group 3 Nal/Mor | Group 4 Cmpd/Mor (0.1 mg/kg) | Group 5 Cmpd/Mor (0.3 mg/kg) | Group 6 Cmpd/Mor (1 mg/kg) |
|---|---|---|---|---|---|---|
| Ex. 1 | 1.028 | 9.361 | 2.496 | 8.870 | 6.907 | 6.240 |
| Ex. 3 | 0.887 | 8.261 | 3.013 | 6.947 | 5.853 | 6.537 |

The results demonstrate that the compounds of Example 1 and Example 3 both exert a dose-dependent blockade of morphine-induced mu-opiate receptor activity.

Example 8: CNS Phosphoprotein Profile

A comprehensive molecular phosphorylation study is also carried out to examine the central nervous system (CNS) profile of the compounds of Example 1 and Example 3. The extent of protein phosphorylation for selected key central nervous system proteins is measured in mice nucleus accumbens. Examined proteins include ERK1, ERK2, Glu1, NR2B and TH (tyrosine hydroxylase), and the compounds of Example 1 and 3 were compared to the antipsychotic agents risperidone and haloperidol.

Mice were treated with the compound of Example 1 or 3 at 3 mg/kg, or with haloperidol at 2 mg/kg. Mice were killed 30 minutes to 2 hours post-injection by focused microwave cranial irradiation, which preserves brain phosphoprotein as it exists at the time of death. Nucleus accumbens was then dissected from each mouse brain, sliced and frozen in liquid nitrogen. Samples were further prepared for phosphoprotein analysis via SDS-PAGE electrophoresis followed by phosphoprotein-specific immunoblotting, as described in Zhu H, et al., Brain Res. 2010 Jun. 25; 1342:11-23. Phosphorylation at each site was quantified, normalized to total levels of the protein (non-phosphorylated), and expressed as percent of the level of phosphorylation in vehicle-treated control mice.

The results demonstrate that neither the compound of Example 1 nor of Example 3 has a significant effect on tyrosine hydroxylase phosphorylation at Ser40 at 30 minutes or 60 minutes, in contrast to haloperidol which produces a greater than 400% increase, and risperidone which produces a greater than 500% increase, in TH phosphorylation. This demonstrates that inventive compounds do not disrupt dopamine metabolism.

The results further demonstrate that neither the compound of Example 1 nor of Example 3 has a significant effect on NR2B phosphorylation at Tyr1472 at 30-60 minutes. The compounds produce a slight increase in GluR1 phosphorylation at Ser845, and a slight decrease in ERK2 phosphorylation at Thr183 and Tyr185.

Example 9: Mouse Marble-Burying Study (OCD Model)

The marble burying test is used to measure repetitive and anxiety-related behavior in rodents. It is based on the observation that rats and mice will bury either harmful or harmless objects in their bedding, and it has been used as an animal model to measure the effect of pharmacological interventions in treatment of repetitive behavior disorders, such as OCD.

Mice are first divided up into four treatment groups: (1) vehicle negative control, (2) 0.3 mg/kg compound of Example 3, (3) 1.5 mg/kg compound of Example 3, and (4) 20 mg/kg MPEP (2-methyl-6-(phenylethynyl)pyridine) positive control. MPEP is a selective mGluR5 glutamate receptor antagonist. Mice in groups (2) and (3) are orally administered the compound of Example 3 at the stated dosage in a 0.5% methylcellulose aqueous vehicle 30 minutes prior to the test. Mice in groups (1) are orally administered the vehicle, and mice in group (4) are given an intraperitoneal injection of MPEP just prior to the start of the test.

The test is conducted in rectangular cages with 4-5 cm of wood chip bedding in a room with the window shades lowered and the door closed to minimize distractions. Fifteen clean marbles are evenly spaced on top of the bedding in three rows of five marbles. One mouse is placed in each cage. The mouse and cage is left undisturbed for 30 minutes. At the end of the test, the mouse is removed and the number of marbles buried to at least ⅔ of their depth is counted. The results are shown in the following table:

| Group | Marbles Buried |
|---|---|
| (1) Vehicle | 13.2 |
| (2) 0.3 mg/kg Ex. 3 | 9.3 |
| (3) 1.5 mg/kg Ex. 3 | 4.7 |
| (4) MPEP | 0.2 |

The results demonstrate that compared to the control, there is a statistically significant decrease in marble burying for the mice treated with 0.3 mg/kg of the compound of Example 3 ($p<0.01$) and with 1.5 mg/kg of the compound of Example 3 ($p<0.001$). In addition, there is a clear dose-response relationship evident.

Example 10: Mu-Opiate Receptor Activity Assays

The compounds of Example 1 and 3 are tested in CHO-K1 cells expressing hOP3 (human mu-opiate receptor μ1 subtype) using an HTRF-based cAMP assay kit (cAMP Dynamic2 Assay Kit, from Cisbio, #62AM4PEB). Frozen cells are thawed in a 37° C. water bath and are resuspended in 10 mL of Ham's F-12 medium containing 10% FBS. Cells are recovered by centrifugation and resuspended in assay buffer (5 nM KCl, 1.25 mM $MgSO_4$, 124 mM NaCl, 25 mM HEPES, 13.3 mM glucose, 1.25 mM $KH_2PO_4$, 1.45 mM $CaCl_2$, 0.5 g/L protease-free BSA, supplemented with 1 mM IBMX). Buprenorphine, a mu-opiate receptor partial agonist, and naloxone, a mu-opiate receptor antagonist, and DAMGO, a synthetic opioid peptide full agonist, are run as controls.

For agonist assays, 12 μL of cell suspension (2500 cells/well) are mixed with 6 μL forksolin (10 μM final assay concentration), and 6 μL of the test compound at increasing concentrations are combined in the wells of a 384-well white plate and the plate is incubated for 30 minutes at room temperature. After addition of lysis buffer and one hour of further incubation, cAMP concentrations are measured according to the kit instructions. All assay points are determined in triplicate. Curve fitting is performed using XLfit software (IDBS) and $EC_{50}$ values are determined using a 4-parameter logistic fit. The agonist assay measures the ability of the test compound to inhibit forskolin-stimulated cAMP accumulation.

For antagonist assays, 12 μL of cell suspension (2500 cells/well) are mixed with 6 μL of the test compound at increasing concentrations, and combined in the wells of a 384-well white plate and the plate is incubated for 10 minutes at room temperature. 6 μL of a mixture of DAMGO (D-Ala$^2$-N-MePhe$^4$-Gly-ol-enkephelin, 10 nM final assay concentration) and forksolin (10 μM final assay concentration) are added, and the plates are incubated for 30 minutes at room temperature. After addition of lysis buffer, and one hour of further incubation, cAMP concentrations are measured according the kit instructions. All assay points are determined in triplicate. Curve fitting is performed using XLfit software (IDBS) and $IC_{50}$ values are determined using a 4-parameter logistic fit. Apparent dissociation constants ($K_B$) are calculated using the modified Cheng-Prusoff equation. The antagonist assay measures the ability of the test compound to reverse the inhibition of forskolin-induced cAMP accumulation caused by DAMGO.

Figure 2:
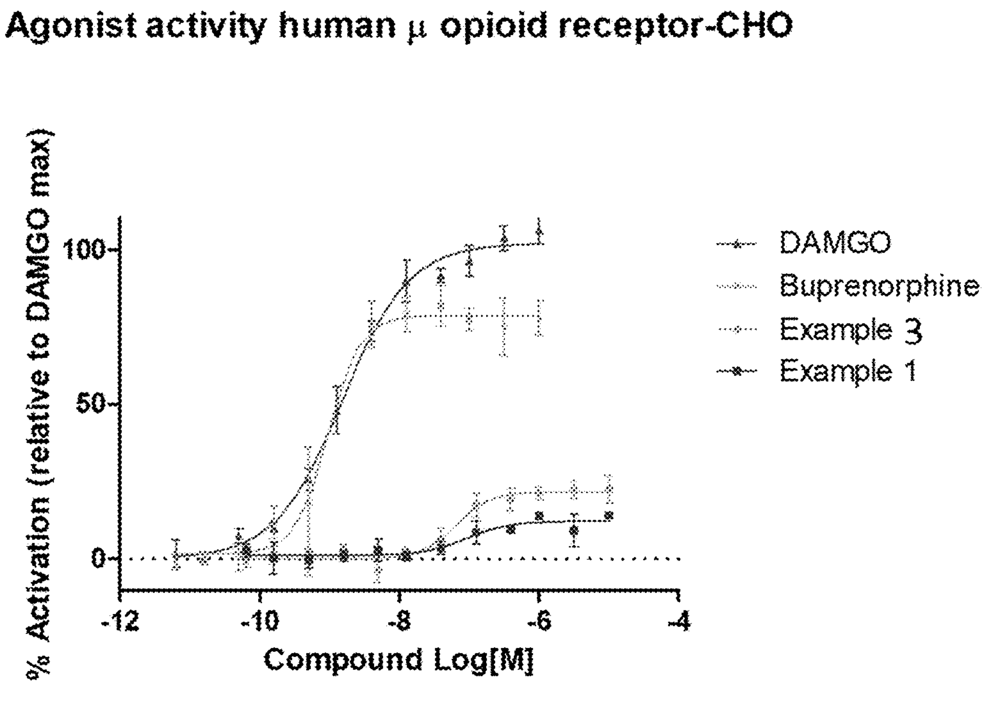
FIG. 2 shows the mu-receptor agonist activity of the compounds of Examples 1 and 3 compared to DAMGO and buprenorphine, as described in Example 10.

The results are shown in FIGS. 1 and 2, and in the Table below. The results demonstrate that the compound of Example 3 is a weak antagonist of the Mu receptor, showing much higher $IC_{50}$ compared to naloxone, and that it is a moderately strong partial agonist, showing about 22% activity relative to DAMGO (as compared to about 79% activity for buprenorphine relative to DAMGO). The compound of Example 1 is also shown to have moderately strong partial agonist activity.

| Compound | Antagonist IC50 (nM) | Agonist EC50 (nM) | KB (nM) |
|---|---|---|---|
| Naloxone | 5.80 | — | 0.65 |
| DAMGO | — | 1.56 | — |
| Buprenorphine | — | 0.95 | — |
| Cmpd. Ex. 3 | 641 | 64.5 | 71.4 |
| Cmpd Ex. 1 | — | 140 | — |

Buprenorphine is a drug used for chronic pain treatment and for opiate withdrawal, but it suffers from the problem that users can become addicted due to its high partial agonist activity. To offset this, the commercial combination of buprenorphine with naloxone is used (sold as Suboxone). Without being bound by theory, it is believed that the compounds of the present invention, which are weaker partial Mu agonists than buprenorphine, with some moderate antagonistic activity, will allow a patient to be more effectively treated for pain and/or opiate withdrawal with lower risks of addiction.

Column 29, Line 18-30:
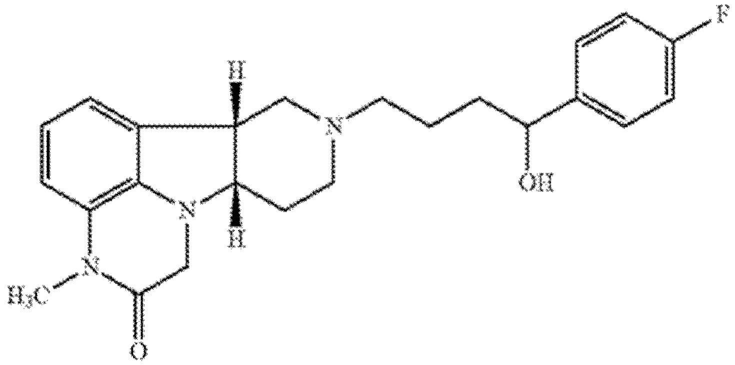
Should be changed to:
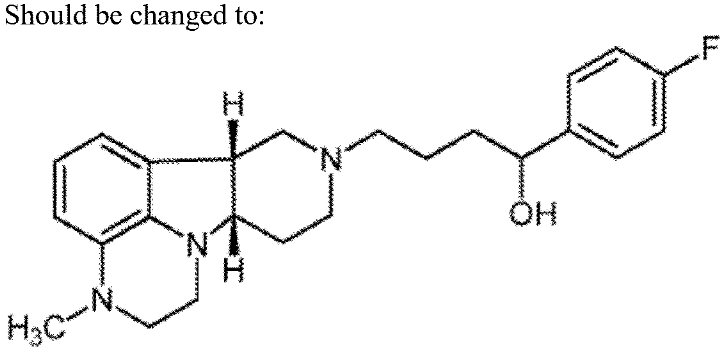
Column 40, Line 17-40:
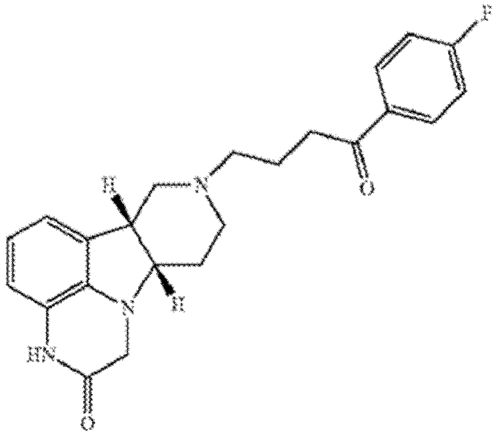
Should be changed to:
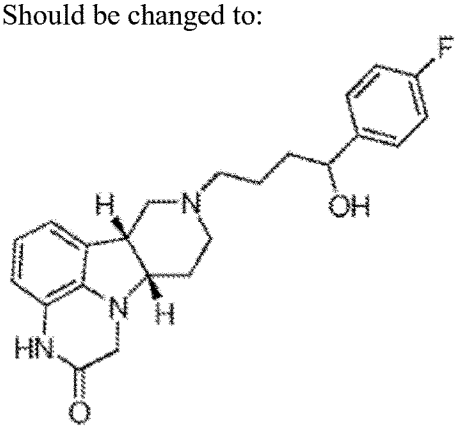

What is claimed:

1. A method for the treatment of a central nervous system disorder, comprising administering to a patient in need thereof a compound of a Formula I:

Formula I

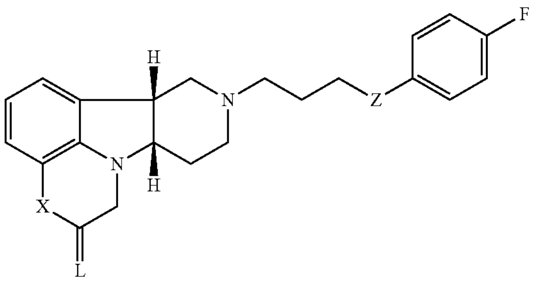

wherein:

X is —NH—;

L is O;

Z is —O— or —C(O)—;

in free or salt form;

wherein the disorder is selected from the group consisting of obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, attention deficit-hyperactivity disorder (ADHD), attention deficit disorder (ADD), impulse control disorder, pain disorders, cephalic pain, neuropathic pain, idiopathic pain, chronic pain, fibromyalgia, chronic fatigue, opiate dependency, cocaine dependency, amphetamine dependency, alcohol dependency, and combinations thereof.

2. The method according to claim 1, wherein the compound is:

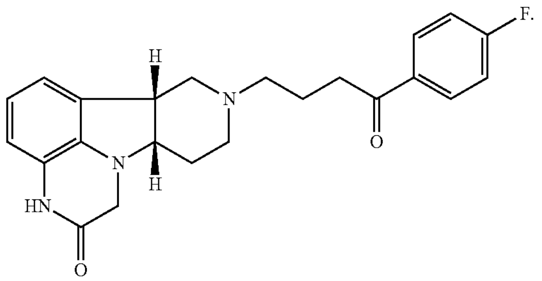 [SMILES: O=C1CN2c3c(cccc3[C@@H]3CN(CCCC(=O)c4ccc(F)cc4)CC[C@@H]32)N1]

3. The method according to claim 1, wherein the compound is:

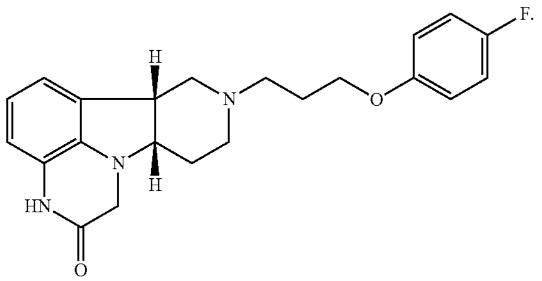 [SMILES: O=C1CN2c3c(cccc3[C@@H]3CN(CCCOc4ccc(F)cc4)CC[C@@H]32)N1]

4. The method according to claim 1, wherein the compound is in the form of a pharmaceutically acceptable salt.

5. The method according to claim 1, wherein the compound is administered to the patient in the form of a pharmaceutically acceptable composition comprising the compound in free or pharmaceutically acceptable salt form, in admixture with a pharmaceutically acceptable diluent or carrier.

6. The method of claim 5, wherein the pharmaceutically acceptable diluent or carrier comprises a polymeric matrix.

7. The method according to claim 6, wherein the polymeric matrix is a biodegradable poly(d,l-lactide-co-glycolide) microsphere.

8. The method according to claim 1 wherein the central nervous system disorder is selected from obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania, attention deficit-hyperactivity disorder (ADHD), attention deficit disorder (ADD) and impulse control disorder.

9. The method according to claim 8, wherein the central nervous system disorder is obsessive-compulsive disorder (OCD) or obsessive-compulsive personality disorder (OCPD).

10. The method according to claim 1, wherein said patient is not responsive to or cannot tolerate the side effects from treatment with selective serotonin reuptake inhibitors (SSRIs).

11. The method according to claim 10, wherein the selective serotonin reuptake inhibitor (SSRI) is selected from the group consisting of citalopram, escitalopram, fluoxetine, fluvoxamine, paroxetine, and sertraline.

12. The method according to claim 1, wherein said patient is not responsive to or cannot tolerate the side effects from treatment with serotonin-norepinephrine reuptake inhibitors (SNRIs).

13. The method according to claim 12, wherein the serotonin-norepinephrine reuptake inhibitor (SNRI) is selected from the group consisting of venlafaxine, sibutramine, duloxetine, atomoxetine, desvenlafaxine, milnacipran, and levomilnacipran.

14. The method according to claim 1, wherein said patient is not responsive to or cannot tolerate the side effects from treatment with antipsychotic agents.

15. The method according to claim 14, wherein the antipsychotic agent is selected from the group consisting of clomipramine, risperidone, quetiapine and olanzapine.

* * * * *

UNITED STATES PATENT AND TRADEMARK OFFICE

CERTIFICATE OF CORRECTION

PATENT NO. : 10,245,260 B2
APPLICATION NO. : 15/660615
DATED : April 2, 2019
INVENTOR(S) : Wei Yao et al.

It is certified that error appears in the above-identified patent and that said Letters Patent is hereby corrected as shown below:

In the Specification

Column 29, Line 4-17:

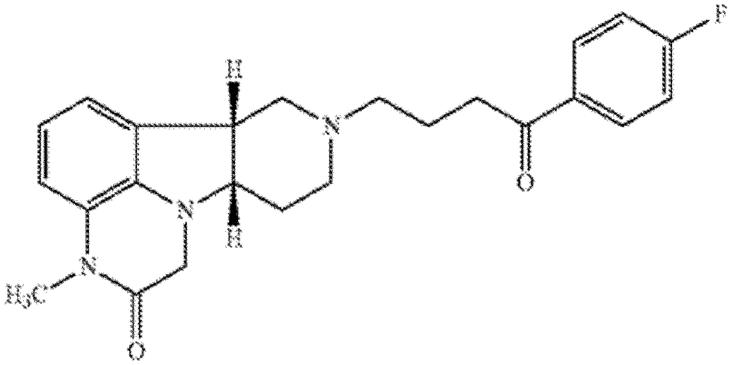

Should be changed to:

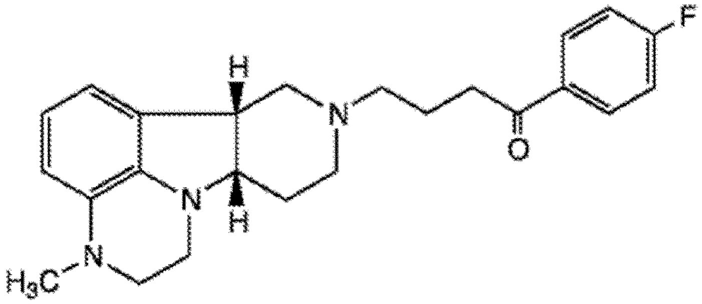

Signed and Sealed this
Sixteenth Day of May, 2023

Katherine Kelly Vidal
*Director of the United States Patent and Trademark Office*